US009962521B2

(12) United States Patent
Kizhakkedathu et al.

(10) Patent No.: US 9,962,521 B2
(45) Date of Patent: May 8, 2018

(54) SHAPE MEMORY MATERIALS BY SURFACE MODIFICATION

(75) Inventors: Jayachandran N. Kizhakkedathu, New Westminster (CA); Yuquan Zou, Richmond (CA); A. Srikantha Phani, Vancouver (CA); Donald E. Brooks, Vancouver (CA)

(73) Assignee: University of British Columbia, Vancouver (CA)

( * ) Notice: Subject to any disclaimer, the term of this patent is extended or adjusted under 35 U.S.C. 154(b) by 1236 days.

(21) Appl. No.: 13/997,036

(22) PCT Filed: Feb. 3, 2012

(86) PCT No.: PCT/CA2012/050060
§ 371 (c)(1),
(2), (4) Date: Jun. 21, 2013

(87) PCT Pub. No.: WO2012/139214
PCT Pub. Date: Oct. 18, 2012

(65) Prior Publication Data
US 2013/0303981 A1    Nov. 14, 2013

Related U.S. Application Data

(60) Provisional application No. 61/474,662, filed on Apr. 12, 2011.

(51) Int. Cl.
*A61M 31/00*    (2006.01)
*A61M 25/00*    (2006.01)
(Continued)

(52) U.S. Cl.
CPC ....... *A61M 25/0045* (2013.01); *A61L 29/041* (2013.01); *A61L 29/085* (2013.01);
(Continued)

(58) Field of Classification Search
CPC .......... A61M 25/0009; A61M 25/0141; A61M 25/005; A61M 25/0012
(Continued)

(56) References Cited

U.S. PATENT DOCUMENTS 6,872,433 B2    3/2005 Seward et al.
7,638,930 B1    12/2009 Kudoh
(Continued)

FOREIGN PATENT DOCUMENTS

AU    2009322136 A1    6/2010
CA    2661766 A1    10/2007
(Continued)

OTHER PUBLICATIONS

International Search Report and Written Opinion for PCT/CA2012/050060 dated Jun. 18, 2012.
(Continued)

*Primary Examiner* — Phillip Gray
(74) *Attorney, Agent, or Firm* — Pepper Hamilton LLP

(57) ABSTRACT

Devices including a flexible substrate and a grafted polymer brush coating on at least one surface of the flexible substrate and methods for making and using such devices are provided herein. The grafted polymer brush included on the devices allow for controlled bending of the device during use.

20 Claims, 25 Drawing Sheets

(51) Int. Cl.
| | |
|---|---|
| A61M 25/01 | (2006.01) |
| A61L 29/04 | (2006.01) |
| A61L 29/08 | (2006.01) |
| A61L 29/16 | (2006.01) |
| A61L 31/04 | (2006.01) |
| A61L 31/10 | (2006.01) |
| A61L 31/16 | (2006.01) |
| A61B 17/06 | (2006.01) |
| A61B 17/064 | (2006.01) |
| A61B 17/122 | (2006.01) |
| A61B 17/00 | (2006.01) |
| A61B 90/00 | (2016.01) |

(52) U.S. Cl.
CPC ............ A61L 29/16 (2013.01); A61L 31/048 (2013.01); A61L 31/10 (2013.01); A61L 31/16 (2013.01); A61M 25/0009 (2013.01); A61M 25/0158 (2013.01); A61B 17/064 (2013.01); A61B 17/06166 (2013.01); A61B 17/122 (2013.01); A61B 2017/00526 (2013.01); A61B 2017/00623 (2013.01); A61B 2017/00858 (2013.01); A61B 2017/00867 (2013.01); A61B 2017/00982 (2013.01); A61B 2017/00995 (2013.01); A61B 2090/065 (2016.02); A61L 2300/602 (2013.01); A61L 2400/16 (2013.01); Y10T 428/23979 (2015.04)

(58) Field of Classification Search
USPC .................................................... 604/95.04
See application file for complete search history.

(56) References Cited

U.S. PATENT DOCUMENTS

| | | | |
|---|---|---|---|
| 2007/0224236 A1* | 9/2007 | Boden ..................... | A61L 27/34 424/423 |
| 2007/0244550 A1 | 10/2007 | Eidenschink | |
| 2009/0076476 A1* | 3/2009 | Barbagli .............. | A61B 5/1076 604/500 |
| 2010/0068153 A1* | 3/2010 | Bangera ............... | A61K 9/0009 424/10.1 |
| 2010/0145286 A1 | 6/2010 | Zhang et al. | |
| 2010/0152708 A1 | 6/2010 | Li et al. | |

FOREIGN PATENT DOCUMENTS

| | | |
|---|---|---|
| CA | 2745204 A1 | 6/2010 |
| CA | 2745440 A1 | 6/2010 |
| CN | 102307955 A | 1/2012 |
| EP | 2054097 A2 | 5/2009 |
| EP | 2352796 A1 | 8/2011 |
| EP | 2352797 A2 | 8/2011 |
| JP | 2006-125396 A | 5/2006 |
| JP | 2009530040 A | 8/2009 |
| KR | 20110106866 A | 9/2011 |
| SG | 171882 A1 | 7/2011 |
| WO | WO2007/112020 A2 | 10/2007 |
| WO | WO2007/112020 A3 | 10/2007 |
| WO | WO2009/130233 A1 | 10/2009 |
| WO | WO2010/065958 A1 | 6/2010 |
| WO | WO 2010/065960 A2 | 6/2010 |
| WO | WO 2010065960 A3 | 6/2010 |

OTHER PUBLICATIONS

Balakrishnan et al., Chemical modification of poly(vinyl chloride) resin using poly(ethylene glycol) to improve blood compatibility, *Biomaterials* (Jun. 2005), 26(19):3495-3502 (Abstract).

Balazs et al., Inhibition of bacterial adhesion on PVC endotracheal tubes by RF-oxygen glow discharge, sodium hydroxide and silver nitrate treatments, *Biomaterials* (May 2004), 25(11):2139-2151 (Abstract).

Barbey et al., Polymer Brushes via surface-Initiated Controlled Radical Polymerization: Synthesis, Characterization, Properties, and Applications, *Chem. Rev.* (Oct. 21, 2009), 109(11):5437-5527 (Abstract).

Bellin et al., Polymeric triple-shape materials, *PNAS* (Nov. 28, 2006), 103(48):18043-18047.

Bunsow et al., Polymer Brushes: Routes toward Mechanosensitive Surfaces, *Acc. Chem. Res.* (Dec. 28, 2009), 43(3):466-474 (Abstract).

Choukourov et al., Mechanistic studies of plasma polymerization of allylamine, *J. Phys. Chem. B.* (Dec. 8, 2005), 109(48):23086-23095 (Abstract).

Freund et al., Thin Film Materials, Stress, Defect, Formation and Surface Evolution, Cambridge University Press (Jan. 2004).

Hosono et al., Large-Area Three-Diminsional Molecular Ordering of a Polymer Brush by One-Step Processing, *Science* (Nov. 5, 2010), 330(6005):808-811 (Abstract).

Huber et al., The selection of mechanical actuators based on performance indices, *Proc. R. Soc. Lond. A* (Oct. 8, 1997), 453:2185-2205.

Huck, Responsive polymers for Nanoscale actuation, *Materials Today* (Jul.-Aug. 2008), 11(7-8):24-32 (Abstract).

Ikeda et al., Photomechanics of Liquid-Crystalline Elastomers and Other Polymers, *Angewandte Chemie International Edition* (Jan. 10, 2007), 46(4):506-528 (Abstract).

Kelby et al., Controlled Folding of 2D Au-Polymer Brush Composites into 3D Microstructures, *Advanced Functional Materials* (Jan. 13, 2011 ), 21(4):652-657 (Abstract).

Kelby et al., Controlled Bending of Microscale Au-Polyelectrolyte Brush Bilayers, *Macromolecules* (May 19, 2010), 43(12):5382-5386 (Abstract).

Kim et al., High-Performance Supercapacitors Based on Poly(ionic liquid)-Modified Graphene Electrodes, *ACS Nano.* (Dec. 13, 2010), 5(1):436-442 (Abstract).

Lamba et al., In vitro investigation of the blood response to medical grade PVC and the effect of heparin on the blood response, *Biomaterials* (Jan. 2000), 21(1):89-96 (Abstract).

Lee et al., Polymer Brushes via Controlled, Surface-Initiated Atom Transfer Radical Polymerization (ATRP) from Graphene Oxide, *Macromolecular Rapid Communications* (Nov. 24, 2009), 31(3):281-288 (Abstract).

Lee et al., Three-Diminsional Self-Assembly of Graphene Oxide Platelets into Mechanically Flexible Macroporous Carbon Films, *Angewandte Chemie International Edition* (Nov. 29, 2010), 49(52):10084-10088 (Abstract).

Lendlein et al., Shape-memory polymers as a technology platform for biomedical applications, *Expert Rev. Med. Devices* (2010), 7(3):357-379.

Lendlein et al., Light-induced shape-memory polymers, *Nature* (Apr. 14, 2005), 434:879-882 (Abstract).

Lendlein et al., Biodegradable, Elastic Shape-Memory Polymers for Potential Biomedical Applications, *Science* (Apr. 25, 2002), 296(5573):1673-1676 (Abstract).

Lendlein et al., Shape-Memory Polymers, *Angewandte Chemie International Edition* (Jun. 12, 2002), 41(12):2034-2057 (Abstract).

Lim et al., Lamination of conductive polypyrrole films to poly(tetrafluoroethylene) films via interfacial graft copolymerization, *Journal of Applied Polymer Science* (Feb. 21, 2001), 80(5):716-727 (Abstract).

Manosa et al., Giant solid-state baracaloric effect in the Ni—Mn—In magnetic shape-memory alloy, *Nature Materials* (Apr. 4, 2010), 9:478-481 (Abstract).

McGinty et al., Hydrophilic surface modification of poly(vinyl chloride) film and tubing using physisorbed free radical grafting technique, *Polymer* (Aug. 9, 2008), 49:4350-4357.

Miaudet et al., Shape and Temperature Memory of Nanocomposites with Broadened Glass Transition, *Science* (Nov. 23, 2007), 318(5854):1294-1296 (Abstract).

Rosner et al., Characterisation of the interface of sputter-deposited copper coatings on nitrogen plasma-treated carbon substrates, *Anal Bioanal Chem* (Nov. 2004), 380(5-6):838-842 (Abstract).

(56) References Cited

OTHER PUBLICATIONS

Small et al., Biomedical applications of thermally activated shape memory polymers, *Journal of Materials Chemistry* (Mar. 2, 2010), 20(17):3356-3366 (Abstract).
Stoney, The Tension of Metallic Films Deposited by Electrolysis, *Proc. R. Soc. Lond. A* (Feb. 4, 1909).
Tsujii et al., Structure and Properties of High-Density Polymer Brushes Prepared by Surface-Initiated Living Radical Polymerization, *Advances in Polymer Science* (2006), 197:1-45 (Abstract).
Uyama et al., Low-frictional catheter materials by photo-induced graft polymerization, *Biomaterials* (Jan. 1991), 12(1):71-75 (Abstract).
Wang et al., Plasma pre-treatment of liquid crystal polymer and subsequent metallization by PVD, *Vacuum* (Oct. 24, 2006), 81(3):325-328 (Abstract).
Xie, Tunable polymer multi-shape memory effect, *Nature* (Mar. 11, 2010), 464:267-270 (Abstract).
Xu et al., High performance shape memory polymer networks based on rigid nanoparticle cores, *PNAS* (Apr. 27, 2010), 107(17):7652-7657.
Zou et al., Surface Modification of Polyvinyl Chloride Sheets via Growth of Hydrophilic Polymer Brushes, *Macromolecules* (Apr. 9, 2009), 42(9):3258-3268 (Abstract).
Zou et al., Bending and Stretching Actuation of Soft Materials through Surface-Initiated Polymerization, *Angew. Chem. Int. Ed.* (2011), 50:5116-5119.
Zou et al., Inhibitory Effect of Hydrophilic Polymer Brushes on Surface-Induced Platelet Activation and Adhesion, *Macromolecular Biosciences* (Oct. 15, 2010), 10(12):1432-1443 (Abstract).

\* cited by examiner

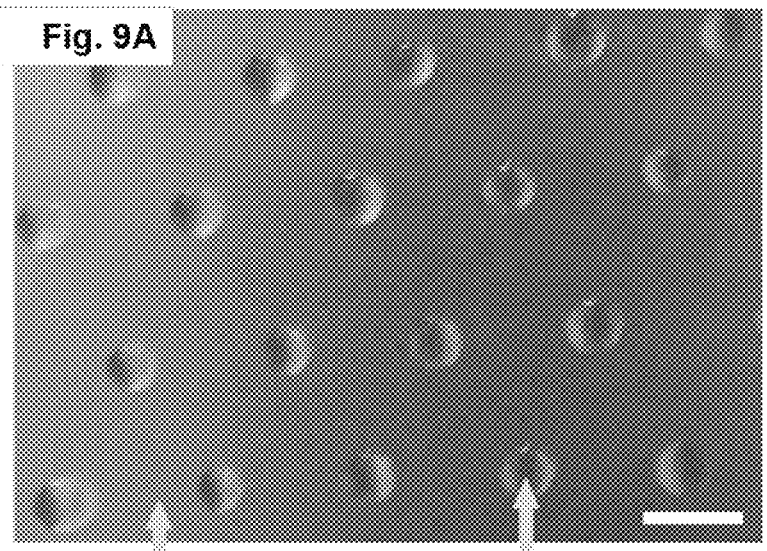
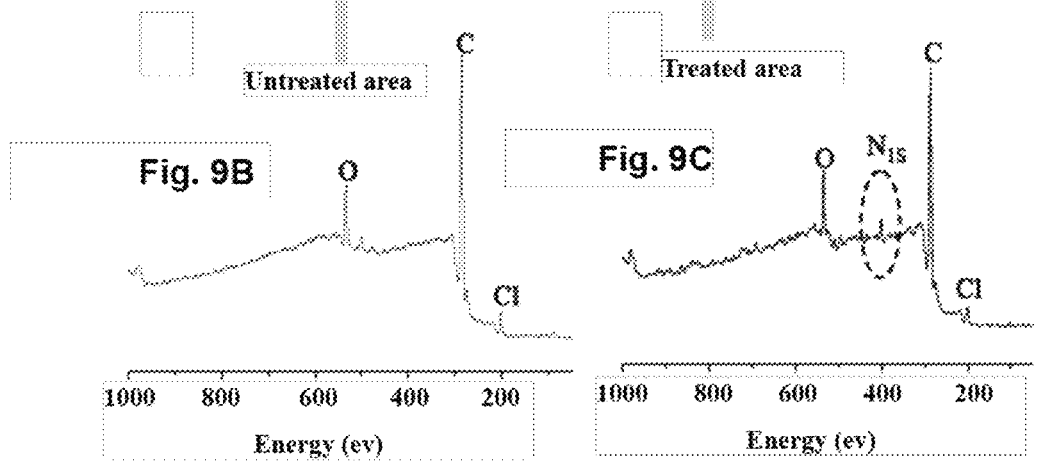

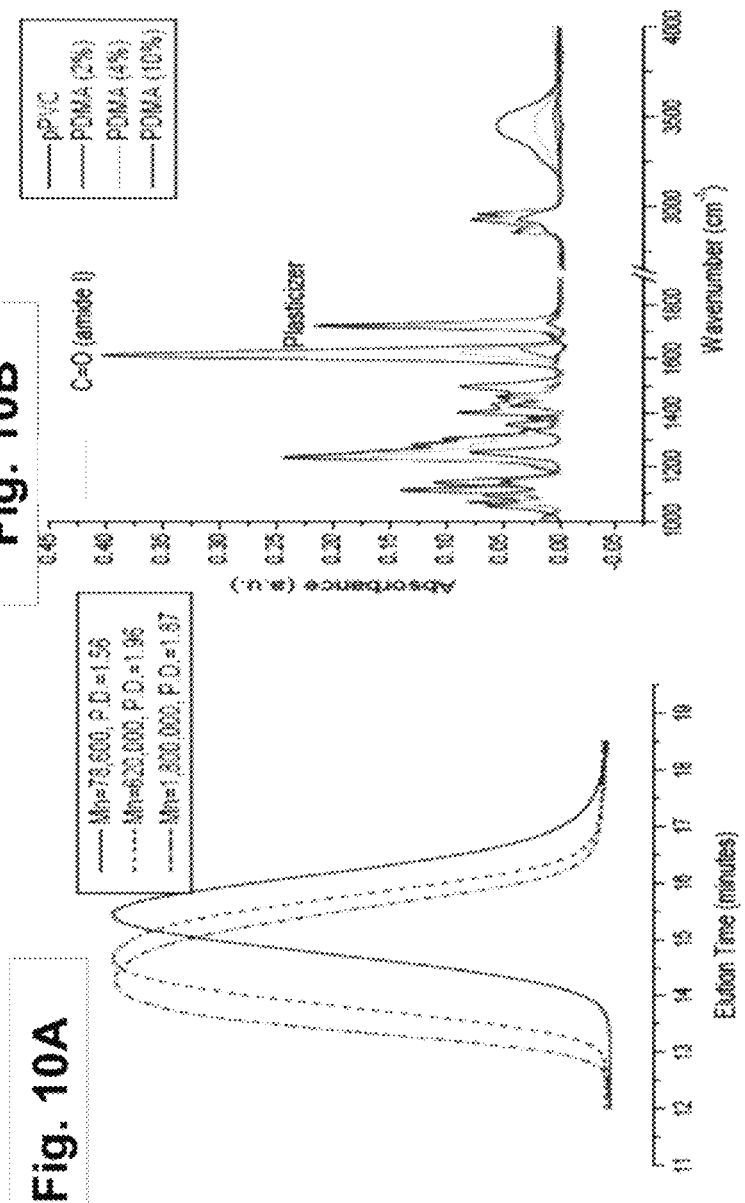

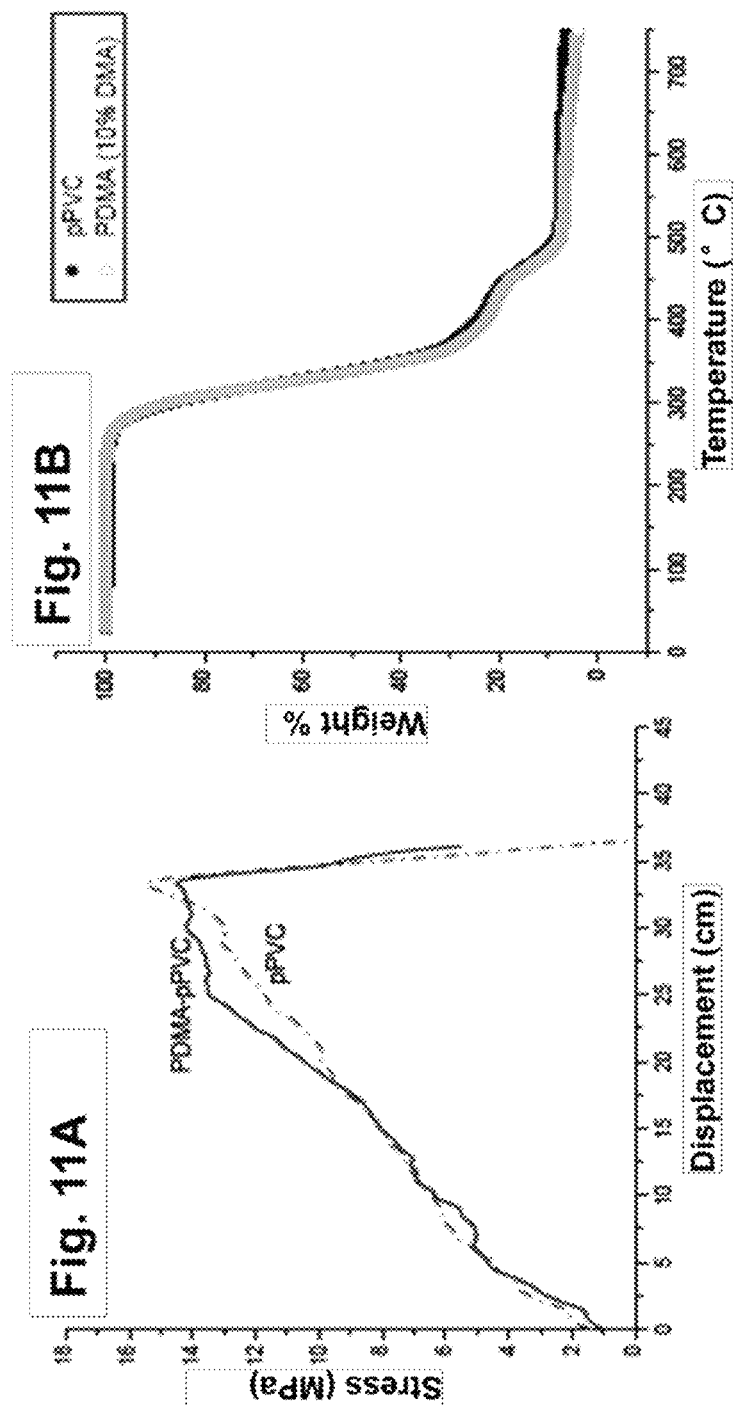

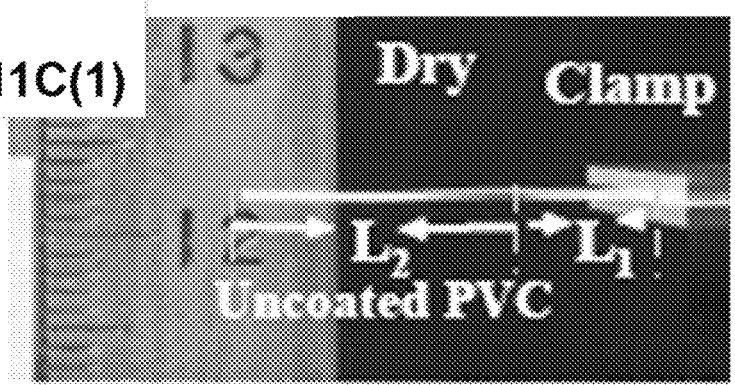
Fig. 11C(1)
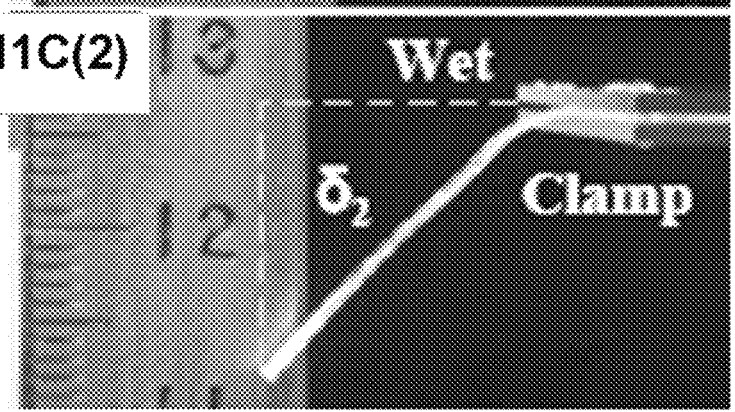
Fig. 11C(2)
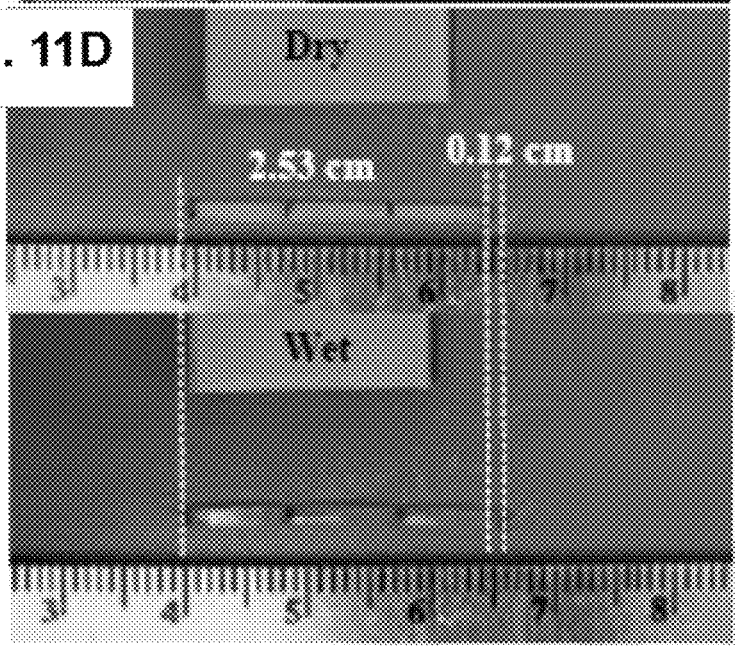
Fig. 11D

United States Patent US 9,962,521 B2

SHAPE MEMORY MATERIALS BY SURFACE MODIFICATION

CROSS-REFERENCE TO RELATED APPLICATIONS

This application is a U.S. National Stage filing under 35 U.S.C. § 371 of International Application No. PCT/CA2012/050060, filed on Feb. 3, 2012 entitled "Shape Memory Materials by Surface Modification," which claims priority to U.S. Provisional Application No. 61/474,662, filed on Apr. 12, 2011, the disclosures of which is hereby incorporated by reference in their entirety.

SUMMARY

Some embodiments described in this disclosure are directed to a device having a flexible substrate and a macroscale grafted polymer brush coating on at least one surface of the flexible substrate. The macroscale grafted polymer brush may allow for controlled bending of the device during use. In some embodiments, the device is a catheter. Other examples of devices include self-tightening sutures, self-retaining sutures, surgical fasteners, stents, aneurysm treatments, clot removal devices, adjustable prosthetic valves, catheter microgrippers, retrieval of devices, dialysis needles, catheters for cell collection by apheresis, anchoring cannula, fertility control devices, implants for hypertension treatment, neuronal electrodes, anchor wires for orthotics or orthodontics, self pealing devices, temperature and light sensitive labels for drugs/vaccines containers, display devices, self-expanding soft structures, and the like.

Some embodiments are directed to a method for delivering therapy to a patient in need of treatment including introducing a device into a vessel of the patient, the device comprising a macroscale grafted polymer brush coating on at least one surface of a flexible substrate; stimulating the grafted polymer brush coating thereby inducing bending of the device; and delivering the therapy.

Some embodiments are directed to a method for preparing a device including providing a device; and applying a macroscale grafted polymer brush to at least one portion of the device. Some embodiments are directed to a kit including a device having a macroscale grafted polymer brush coating on at least one surface of a flexible substrate; and instructions on how to use the device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 9A shows a representative pPVC specimen, covered by stainless steel block with regularly patterned holes, that was treated by allylamine plasma, sonicated in water, and removed for photographing. The scale bar is 1 cm.

FIG. 9B is a representative XPS spectrum of untreated area (survey scan).

FIG. 9C is a representative XPS spectrum of allylamine plasma treated area (survey scan).

FIG. 10A is a representative GPC profile of PDMA formed in SI-ATRP solutions. The three samples shown were obtained in 2%, 5%, and 10% DMA concentration (wt %).

FIG. 10B depicts representative ATR-FTIR spectra of unmodified pPVC and PDMA grafted pPVC prepared under different DMA concentrations.

FIG. 11A depicts representative force-displacement curves of an unmodified pPVC and a PDMA-grafted pPVC (10% DMA, 24 h polymerization) measured by an Instron Universal Testing Machine.

FIG. 11B depicts representative TGA curves of pPVC and PDMA-grafted pPVC (10% DMA, 24 h polymerization).

FIG. 11C(1) is a photograph of PDMA grafted pPVC substrate coated on one side under dry state.

FIG. 11C(2) is a photograph of PDMA grafted pPVC substrate coated on one side under wet state.

FIG. 11D is a photograph of a proof-of-concept stretching actuator based on PDMA brush grafted pPVC sample and illustrates a comparison of length of the pPVC specimen grafted with PDMA on both sides under dry and wet state.

DETAILED DESCRIPTION

Figure 1A:
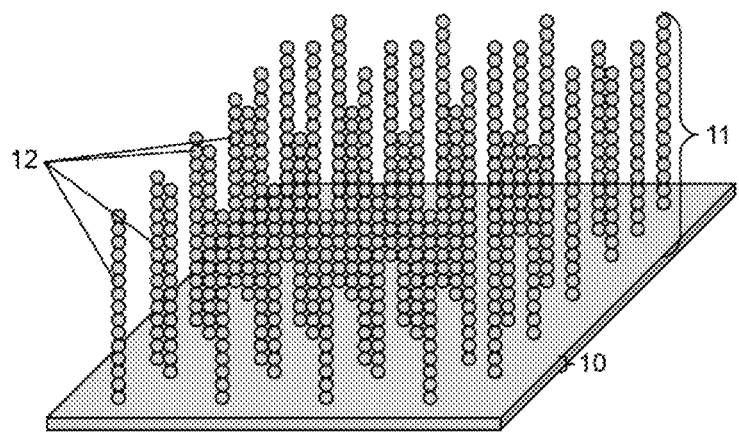
FIG. 1A is an illustrative diagram of a shape memory material having a grafted polymer brush layer on a flexible substrate.

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

The network of arteries in the heart is very difficult to access through a catheter especially at the branching points of arteries. There is no guided catheter system available for allowing the catheter to be guided through the network of arteries, and currently, curved tip catheters are used for this purpose.

Shape-memory materials (SMM) possess the ability to respond to external stimuli such as, for example, temperature, electricity, magnetic field, and light, and change their shape as a result of these stimuli. During this process, the energy from the external stimulus allows the material to mechanically deform which makes them attractive for various applications in biomedical devices, deployable structures, artificial muscle, micro-devices, sensors, and the like. Traditional SMM rely on the properties of bulk material, and polymers, metallic alloys, and composite materials, among other materials, have been used in various SMM applications.

Recently, polymer brush based nanoscale bending actuators have been reported. In these polymer brush-based materials, over-crowded polymer chains were found to be able to exert forces onto an underlying substrate and deform a substrate associated with the polymer brush due to the strong inter-chain repulsion. However, there is no empirical evidence that bending observed in these nanoscale materials can be adapted for use on a macroscale. Furthermore, axial stretching, as well as pure bending, may be required to provide macroscopic actuation.

Various embodiments of the present disclosure are directed to active catheters. An active catheter is a catheter that physicians can control through electro-mechanical means rather than the current manual method. Traditionally, guide wires manipulated externally to the patient are used for guidance of the catheter by combinations of push-pull and torque motions. Limitations of the current catheter and guidewire designs increase procedural time and can cause lumen or vessel wall damage creating subsequent medical complications. These issues become more critical when dealing with narrow and complex passages such as blood vessels in the brain and tertiary bronchi of the lung.

Figures 1B, 1C:
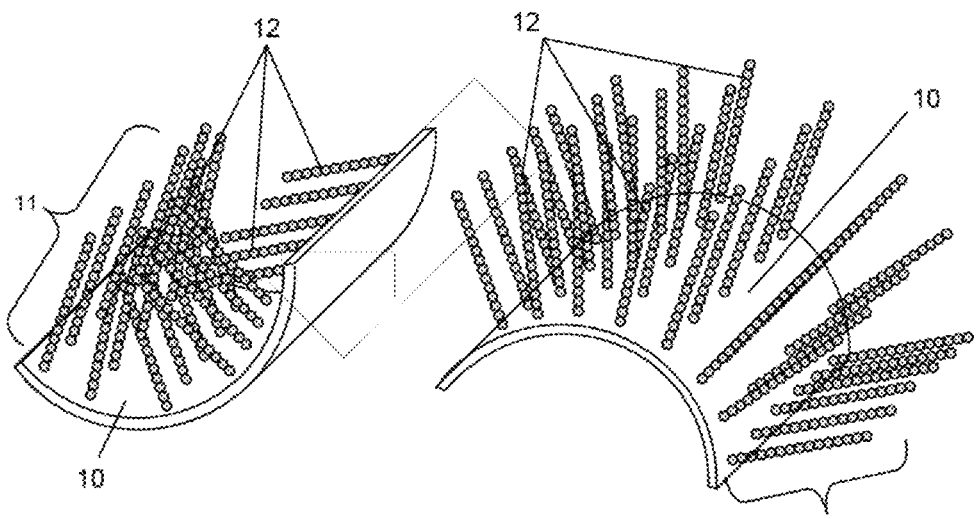
FIG. 1B is an illustrative diagram of the shape memory material of FIG. 1A after bending has been induced by stimulating attraction between individual elements of the grafted polymer brush.
FIG. 1C is an illustrative diagram of the shape memory material of FIG. 1A after bending has been induced by stimulating repulsion of individual elements of the grafted polymer brush.

Some embodiments described herein are directed to devices that include materials that are capable of bending under appropriate stimuli. As illustrated in FIG. 1A, these devices, in general include a flexible substrate layer 10 and a grafted polymer brush layer 11 on at least one surface of the flexible substrate. The polymer brush 11 can be on either a nanoscale or macroscale. Further, the polymer brush 11 may be capable of responding to stimuli that is applied to the grafted polymer brush layer 11 that allows the grafted elements 12, i.e., "bristles" of the grafted polymer layer 11 to interact with one another. For example, the grafted elements 12 of the grafted polymer layer 11 may be attracted to one another under stimuli causing the flexible substrate to contract and bend as illustrated in FIG. 1B or the flexible substrate layer 10 may stretch when a stimuli is applied to the grafted polymer brush layer 11 causing the grafted elements 12 to be repelled from each other as illustrated in FIG. 1C. This bending and stretching may be generally reversible; therefore, a flexible substrate 10 coated with a grafted polymer brush 11 may go back to its original shape after the stimuli has been removed or as the result of a second stimuli on the grafted polymer brush 11.

Devices including the grafted polymer brush layer of embodiments herein have numerous applications and may be particularly suited to applications in which thickness of the substrate or size of the device should be small. Any device in which a thin substrate is required to reversibly bend or that requires thin actuators can be modified to incorporate the materials of embodiments. For example, the materials of the invention may be incorporated into medical devices and other devices that use bendable tubes. The materials of the invention may also be incorporated into mechanical switches and robotic devices such as, for example, artificial muscle and robotic appendages.

Figure 2A:
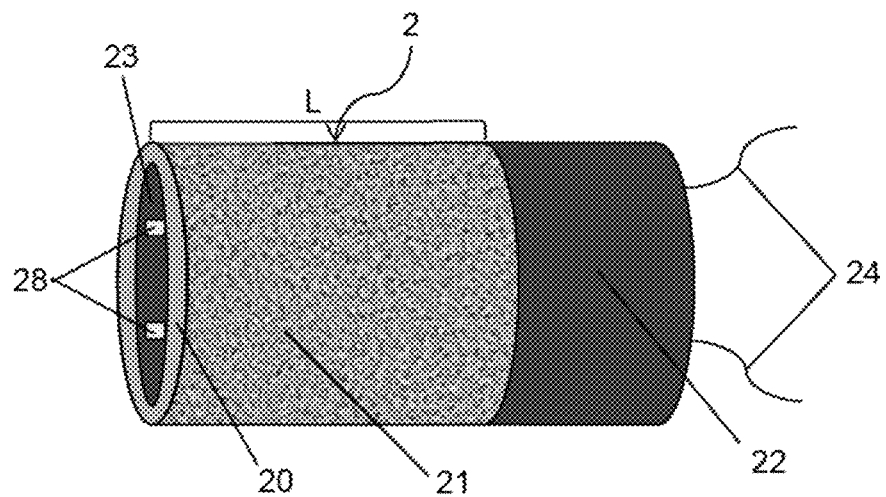
FIG. 2A is an illustrative diagram of a device having a grafted polymer brush layer on an outer surface of the device and stimuli producing elements that heat the grafted polymer brush in the lumen of the device.
Figure 2B:
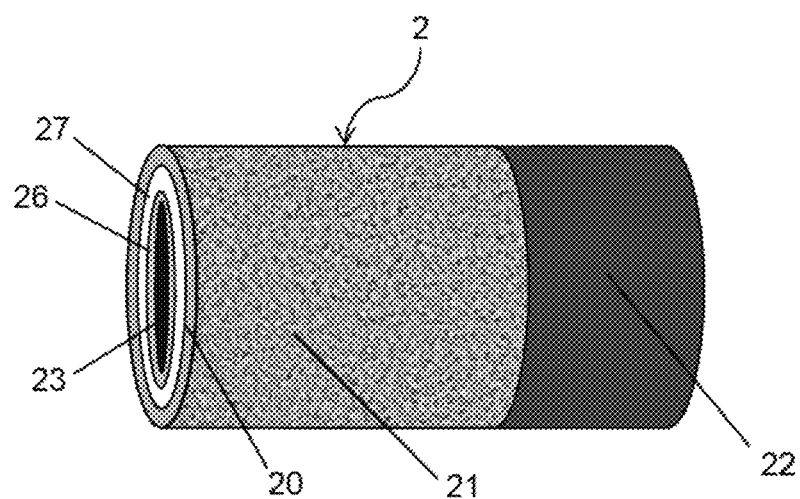
FIG. 2B is an illustrative diagram of a device having a grafted polymer brush layer on an outer surface of the device and a secondary lumen for carrying a stimuli producing liquid to the grafted polymer brush.

Certain embodiments are directed to a smart tip for a catheter, as illustrated in FIGS. 2A and 2B. Such a catheter tip 2 may include a flexible substrate 20 that has been coated with a grafted polymer brush 21. Adjacent uncoated substrate or uncoated portions of the catheter 22 may also be provided. In some embodiments, as illustrated in FIG. 2A, stimuli may be delivered electronically by providing heating elements 28 within the central lumen 23 of the catheter tip 2 that change the temperature of the grafted polymer layer a few degrees in response to an electrical signal causing the catheter tip 2 to bend. Wires or any other means 24 for transmitting an electrical signal the length of the catheter 22 may be used to carry the signal from a control module manipulated by a user to the catheter tip 2. In other embodiments, as illustrated in FIG. 2B, a stimuli may be provided using a liquid. In such embodiments, a central tube 26 can provide a central lumen 23 within the catheter tube 22 and a secondary lumen 27 between the central tube 26 and the catheter tube 22. Liquids may be carried to the catheter tip 2 through the secondary lumen 27 that, for example, change the local pH or salt content of the catheter tip 20 and allow for reversible movement of the catheter tip 2.

The catheter tips of embodiments may be of varying sizes depending on their use and the amount of bending required for their use, and in various embodiments, the catheter tips may include an area that is coated with a grafted polymer brush that is about 1 mm to about 10 cm in length L. For example, in various embodiments, about 1 mm, about 2 mm, about 5 mm, about 10 mm, about 50 mm, about 100 mm, about 1 cm, about 5 cm, about 10 cm, or more or any length between these exemplary lengths can be coated with the grafted polymer. The diameter of the catheter tip may be about the same diameter as any commonly used catheter such as, about 1 mm (3 Fr or "French") to about 12 mm (34 Fr). In some embodiments, the catheter tips may be manufactured to fit any catheter including catheters having diameters 3 Fr, 4 Fr, 5 Fr, 6 Fr, 7 Fr, 8 Fr, 9 Fr, 10 Fr, 11 Fr, 12 Fr, 13 Fr, 14 Fr, 15 Fr, 16 Fr, 17 Fr, 18 Fr, 19 Fr, 20 Fr, 21 Fr, 22 Fr, 23 Fr, 24 Fr, 25 Fr, 26 Fr, 27 Fr, 28 Fr, 29 Fr, 30 Fr, 31 Fr, 32 Fr, 33 Fr, and 34 Fr or ranges between these values. In other embodiments, the catheter tip may be slightly larger than the catheter to which it is attached, for example, about 1.05 mm to about 1.25 mm for a 3 Fr catheter or about 12.05 mm to about 12.5 mm for a 34 Fr catheter. In still other embodiments, the catheter tip may be slightly smaller than a commonly used catheter, for example, about 0.90 mm to about 0.95 mm for a 3 Fr catheter or about 11.75 mm to about 11.95 mm for a 34 Fr catheter. The ranges provided above are for exemplary purposes and larger or smaller tips may be provided for any size catheter.

The term "catheter tip," as used herein, refers to the distal most portion of a catheter that is placed within a vessel by a user such as, without limitation, a surgeon. In general, the tip of the catheter encompasses the area within about 2 mm to about 5 cm of the distal most end of the catheter. With regard to their utility, a catheter tip having a smaller diameter may require a catheter tip having a smaller length than a catheter tip having a larger diameter to produce the same amount of bending. The amount of bending allowed by the tip may also be a function of the length of the catheter tip. For example, tips having a shorter length may allow for bending of about 45° or less whereas catheter tips having longer lengths may allow for being greater than 45° or even 90° or greater or any temperature between these ranges. The catheter tips of various embodiments may be individual components that can be added to an existing catheter or a grafted polymer brush layer may be applied to the tip or a portion of the tip of an existing catheter to produce a catheter with an integral bendable catheter tip.

In further embodiments, several portions of a catheter may be coated with the grafted polymer brush material described above. In such embodiments, the catheter tip may include a flexible substrate and a grafted polymer brush layer that allows for bending when stimulated and one or more portions of the catheter tube other than the tip may be coated with a grafted polymer brush layer to facilitate bending in a central portion of the catheter. Each of the catheter tips and the one or more other portions of the catheter tube coated with the brush polymer layer may be about 1 mm to about 10 cm in length or any value between these ranges, and the various portions of the catheter tube that include the grafted polymer brush layer may be separated by about 1 mm to about 10 cm or any value between these ranges of uncoated catheter. In still other embodiments, one or more portions of a catheter that are proximal from the distal tip of the catheter tube may be coated with a grafted polymer brush layer. For example, a catheter may have an uncoated segment having a length of 1 mm to about 10 cm at the distal most tip followed by a coated segment having a length of about 1 mm to about 10 cm or any value between these ranges.

The catheters and catheter tips described above are generally biocompatible and can be sterilized using known low temperature sterilization (LTS) techniques such as, for example, γ or e-beam irradiation, hydrogen peroxide vapor, low-temperature gas plasma, and ethylene oxide techniques or combinations thereof. While certain embodiments are directed to cardiac and other catheters used in the circulatory system, the tips and catheters described herein can be adopted for any use including, for example, neural or renal catheters. In other embodiments, the grafted polymer brush material can be used in other medical devices including, but not limited to, self-tightening sutures, self-retaining sutures, surgical fasteners, stents, aneurysm treatments, clot removal devices, adjustable prosthetic valves, catheter microgrippers, retrieval of devices, dialysis needles, catheters for cell collection by apheresis, anchoring cannula, fertility control devices, implants for hypertension treatment, neuronal electrodes, anchor wires for orthotics or orthodontics, and the like.

Further embodiments are directed to methods for manipulating a device by providing a manipulable tip or other portion of the device and stimulating the manipulable tip or other portion of the device to produce a bend in the device. The manipulable tip or other portion of the device may be composed of or include a coating of a grafted polymer brush material. In particular embodiments, the device may be a catheter. Still other embodiments are directed to methods for performing a surgical procedure using such devices and methods for making devices, such as catheters and catheter tips that are composed of or have a grafted polymer brush based coating.

The shape-memory materials of various embodiments are based on bending and stretching actuators that have been surface modified with polymeric substrates such as, for example, nanoscale polymer brushes and macroscale polymer brushes. The bending and stretching actuators of such embodiments generally include a flexible substrate 10 that has a polymer that includes a plurality of grafted polymer chains 12 coated on at least one surface resulting in a coating having a brush-like morphology 11, see FIG. 1A. When stimuli, such as, for example, a change in humidity, temperature, pH, or salt concentration is applied to the grafted polymer layer 11, conformational changes associated with individual grafted polymer chains 12 can be produced causing the underlying flexible substrate 10 to bend or stretch, see FIG. 1B and FIG. 1C. Depending on the grafted polymer and the stimuli used to induce bending or stretching, the bending and stretching produced may be nanoscale or macroscale. The force achieved per unit length and actuation strains produced by this bending or stretching may allow the grafted material systems described herein to be used in the preparation of artificial muscle, flexible catheters, and in the design space, various other biomedical and nanotechnology devices.

The substrate material 10 may be any flexible substrate material known and useful in the art. For example, in some embodiments, the flexible substrate 10 may be a polymeric material such as, but not limited to, thermoplastic elastomers (TPE) or other elastomers such as, for example, polyester ethers, copolyester ethers such as ECDEL, styrene based TPE, olefin based TPE, urethane based TPE, ester based TPE, amide based TPE, polyolefins, natural rubber, synthetic rubber, poly (acrylates/methacrylates), hydrogels (synthetic and natural), and silicone rubbers. In certain embodiments, the substrate may be polypropylene, C-FLEX™, LUPOLEN™ 1840H, LUPOLEN™ 3020D, PELLETHANE™ 2363-75D, PELLETHANE™ 2363-55D, TECOTHANE™, CARBOTHANE™, and mixtures of these. In other embodiments, the substrate may be, for example, polyvinyl chloride (PVC), polytetrafluoroethylene (PTFE), polypropylene (PP), polyethylene (PE), or low-density polyethylene (PE-LD). The flexible substrate 10 of various embodiments may be of any desirable thickness and size, which may depend on, for example, the purpose for the device. As is well known in art, flexibility is a function of the thickness of the substrate. Therefore, the thickness may be selected to provide a particular flexibility (i.e., shore value), and in particular embodiments, the shore value may be in the range of about 20 A to about 70 D, or about 40 A to about 100 A or any value between these ranges.

In some embodiments, the surface of the substrate may be modified to allow for polymerization of the memory material on the surface of the substrate, such as the grafted polymer brush 11 described above. Surface modification and building of the polymer brush layer may be carried out by any means known in the art. For example, in certain embodiments, the surface of the flexible substrate 10 may be modified to include one or more reactive groups or initiators that facilitate binding of the polymeric brush to the substrate. The substrate surface and the type of substrate used generally dictates reactive groups that will enable covalent binding of the derivatizing moiety. Examples of reactive groups that can be used to provide a modified surface for the substrate include sulfur-containing functional groups such as thiols, sulfides, disulfides (e.g., —SR or —SSR where R is alkyl, typically lower alkyl, or aryl), and the like; tri-substituted silanes —SiX$_3$ where X is halo or lower alkoxy (typically chloro or methoxy); carboxylic acids; hydroxamic acids; acid chlorides; anhydrides; epoxides; peroxide groups; nitrile groups; thioester groups; alkoxamine groups; ester groups; haloester groups; sulfonyl groups; phosphoryl groups; hydroxyl groups; amino acid groups; amides; and the like and combinations of these.

The shape memory material (SMM) may be any shape memory material known and used in the art. For example, the grafted polymer brush may be a polymer prepared from monomers including, but not limited to, PEG-based monomers such as poly(ethylene glycol) methyl ether acrylate, poly(ethylene glycol) methyl ether methacrylate, poly(ethylene glycol) methyl ether acrylamide, poly(ethylene glycol) methyl ether methacrylamide, poly(vinyl methyl ether), poly (N-vinyl caprolactam), poly(N,N-dimethylacrylamide), poly(N-2,3-dihydroxylpropyl)acrylamide, poly(2,2-dimethyl-1,3-dioxalane)methyl] acrylamide, polydodecyl methacrylate (PDMA), dodecyl methacrylate (DMA), poly-n-butyl acrylate (PnBA), styrene/acrylonitrile copolymer (AS), polypropylene-polymethyl methacrylate (PMMA), neutral hydrophilic monomers such as acrylamide. N-acryloylmopholine, 2-hydroxyethyl methacrylate (HEMA), N-isopropylacrylamide (NIPAM), 2-methoxyethyl acrylate (MEA), 2-methacryroyloxyethylphosphorylcholine (MPC), acrylamide/methacrylamide derivatives of carbohydrates. [3-(Methacryloylamino) propyl]dimethyl(3-sulfopropyl) ammonium hydroxide (SBMA), 1-vinyl-2-pyrrolidone (VP), basic monomers such (3-acrylamidopropyl)trimethylammonium (APTA), allylamine (AA), 1,4-diaminobutane methacrylamide (DABMA), acidic such as 2-acrylamido-2-methyl-1-propanesulfonic acid (AMPS), ethylene glycol methacrylate phosphate (EGMP), hydrophobic monomer such as 2,2,2-trifluoroethyl methacrylate (TFEM), light sensitive polymer such as azobenzene containing copolymers of poly(ethyleneglycol) methacrylate, temperature sensitive polymers of N-substituted acrylamides/methacrylamides (PAM) and various combinations of these. Of course, other polymers capable of being used to prepare the SMM described herein are also encompassed by embodiments of the invention. In particular embodiments, the SMM may be polydodecyl methacrylate (PDMA).

The SMM may be applied to the substrate to form a grafted polymer coating. While SMM may be applied to form a coating having any morphology, in certain embodiments, the SMM may have brush morphology as illustrated in FIG. 1A, such as known nanoscale polymer brushes and macroscale polymer brushes. The grafted polymer coating may be provided over one or more portions of the device or over the entire outer surface of the device. For example, in some embodiments, the grafted polymer may be provided on or near the tip of a device such as a catheter, as illustrated in FIGS. 2A and 2B, to allow the tip to bend as the device is inserted into, for example, a vein or artery. In other embodiments, the portions of the device may be coated with the grafted polymer SMM to provide specific areas where the device is capable of bending. For example, the device may be coated on or near the tip and away from the tip but within one or more millimeters or one or more centimeters to provide a location for secondary bending, which may provide further improved control of the device during insertion.

Devices encompassed by embodiments of the present disclosure may further include additional grafted elements that may be necessary to initiate bending. These additional grafted elements may generally provide localized changes in, for example, humidity, temperature, light, or pH which provide stimuli to the grafted polymer allowing conformational changes associated with grafted polymer chains to occur resulting in bending. For example, in some embodiments, the additional grafted elements may be simple heating elements 28 in FIG. 2A that are capable of providing a localized change in temperature. Such heating elements 28 can be provided below the substrate 20 and within the lumen 23 of, for example, a catheter 22.

Depending on the use and size of the device, the localized area may be an area of, for example, one or more square millimeters or micrometers for small catheters, or one or more square centimeters for larger devices that can be used for endoscopy. The size of the localized area may further depend on the amount of bending required for a particular device. Initiation of larger bends of, for example, 30° to 90° may require a larger area of localized heating than smaller bends of, for example, less than 30°. The skilled artisan may adjust the area heated based on the amount of heat provided to the heating element or the size of the heating element itself and can determine the appropriate size and shape for the heating element based on the criteria discussed above. In some embodiments, the devices of the invention can be used in cardiac catheters, and in other embodiments, the devices including the SMM materials of various embodiments may be adapted for implantation or insertion into the coronary vasculature, peripheral vascular system, esophagus, trachea, colon, biliary tract, urinary tract, prostate, brain, or any combination of these.

Figure 3A:
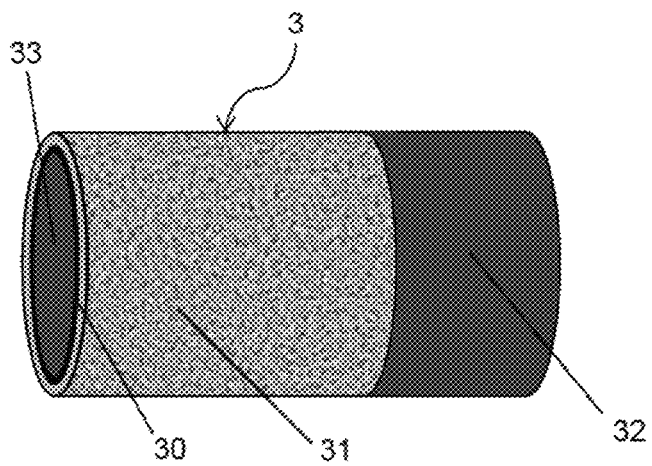
FIG. 3A is an illustrative diagram of a device having a graft polymer brush layer on an outer surface of the device.
Figure 3B:
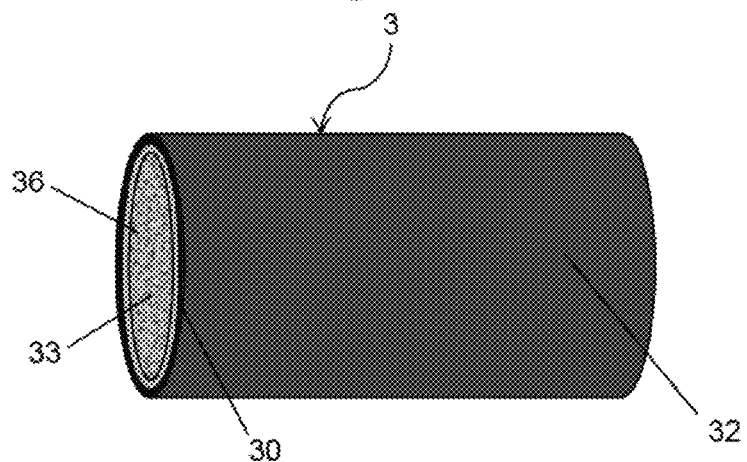
FIG. 3B is an illustrative diagram of a device having a graft polymer brush layer on an inner surface of the device.

Certain embodiments, as illustrated in FIG. 3A, are directed to catheters 3 including a tube of size and shape consistent with catheters known in the art that include a flexible substrate 30. The tube 32 may be made from any material identified hereinabove as a substrate material and may be functionalized in any manner described above. The tube 32 further provides a lumen 33. In such embodiments, an outer surface FIG. 3A, an inner surface FIG. 3B, or both an outer and an inner surface FIG. 3C of the tube 32 can be coated with a grafted polymer SMM 31/36. The grafted polymer 31/36 may be prepared from any of the materials described above. Localized bending may be accomplished by providing grafted elements 28 such as those depicted in FIG. 2 that are capable of changing the local environment of the tube and the local morphology of the grafted polymer, thereby inducing bending at certain locations along the tube. In other embodiments, the coating may be provided at one or more portions of an outer 41, inner 46, or both inner and outer surfaces of a tube 42 that provides a flexible substrate 40 to provide patches that allow particular sections of the catheter 4 to bend, see FIG. 4.

The catheters of such embodiments may further include one or more stimuli producing elements 28 of FIGS. 2A and 2B that stimulate the grafted polymer. In some embodiments, the stimuli producing elements 28 may be provided throughout the length of the catheter and, in other embodiments, stimuli producing elements may be attached to specific locations within the device. In still other embodiments, the stimuli producing elements 28 may be movable, such that their location can be changed within the device to provide localized stimuli at different locations throughout use. Movement can be accomplished, for example, by providing wires 24 attached to the stimuli producing elements 28 that can be shortened or lengthened during use to pull the stimuli producing elements proximally away from the tip of the device or push the stimuli producing elements distally toward the tip of the device. In some embodiments, grooves into which the stimuli producing elements can be placed may be machined within the lumen of the device to further facilitate movement of the stimuli producing elements 28 during use.

Figure 3C:
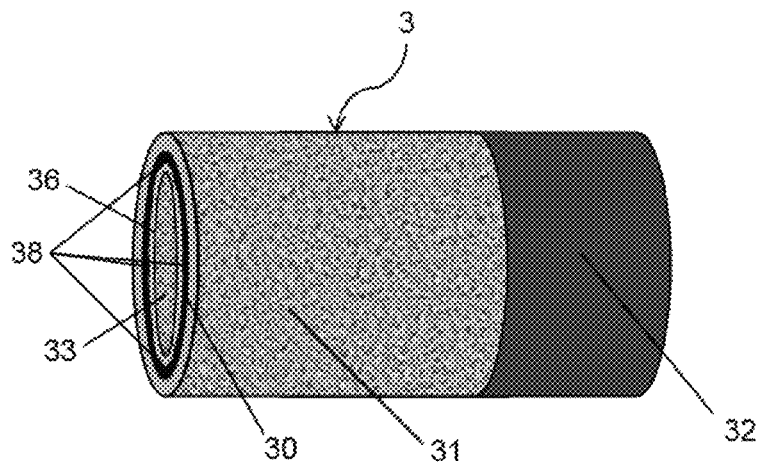
FIG. 3C is an illustrative diagram of a device having a graft polymer brush layer on an outer and an inner surface of the device.
Figure 4:
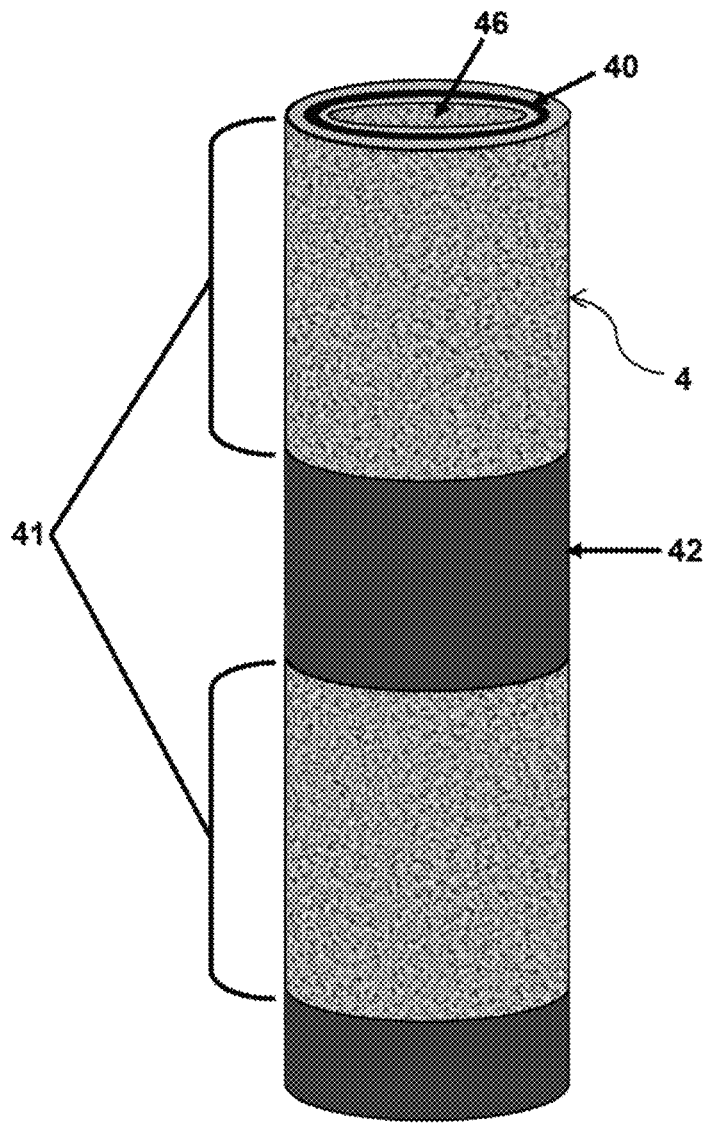
FIG. 4 is an illustrative diagram of a device having a graft polymer brush layer on outer and inner surfaces of the device in which two portions of the device are coated with a graft polymer brush.

The stimuli producing elements 28 may generally be contained within the lumen of a catheter 22 as illustrated in FIG. 2A and may contact an inner surface of the catheter 22 at any location within the tube. In particular embodiments, the stimuli producing elements may be adjacent the flexible substrate layer 20 and opposite the grafted polymer layer 21 of the device. In embodiments in which the device includes an inner and outer grafted polymer layers as illustrated in FIG. 3C, stimuli producing elements 38 may be positioned between an outer grafted polymer layer 31 and the inner grafted polymer layer 36. In some embodiments, an arrangement including outer and inner grafted polymer layers may include two separate flexible substrate layers, a first flexible substrate associated with the outer grafted polymer layer and a second associated with an inner grafted polymer layer. The stimuli producing elements may be positioned between the first and second flexible substrates. The stimuli producing elements between layers may stimulate both grafted polymer layers individually, and in some embodiments, first stimuli producing elements for stimulating the outer grafted polymer layer may be associated with the first flexible substrates and separate second stimuli producing elements for stimulating the inner grafted polymer layer may be associated with the second flexible substrate.

Stimuli producing elements may provide any form of stimuli to the grafted polymer layer. For example, in some embodiments, the stimuli producing elements may heat the substrate in one or more location on or near the grafted polymer layer. Embodiments including such stimuli producing elements are exemplified in FIG. 2A and FIG. 3C. In other embodiments, the stimuli producing element may deliver a fluid that changes the local environment of the grafted polymer by, for example, increasing a salt concentration or increasing or decreasing the pH. Such a stimuli producing element is exemplified by the secondary lumen 27 of FIG. 2B. The stimuli producing elements may be permanently attached to the substrate at one or more positions within the catheter or, in some embodiments, stimulating grafted elements may be capable of being moved, within the device, to provide different areas of localized stimuli at various locations within the device. In still other embodiments, stimuli producing elements may be provided throughout the length of the catheter but may be configured to produce localized stimuli. In yet other embodiments, the catheters may include other conventional components used to guide the catheter such as, for example, a guide wire.

Figure 5:
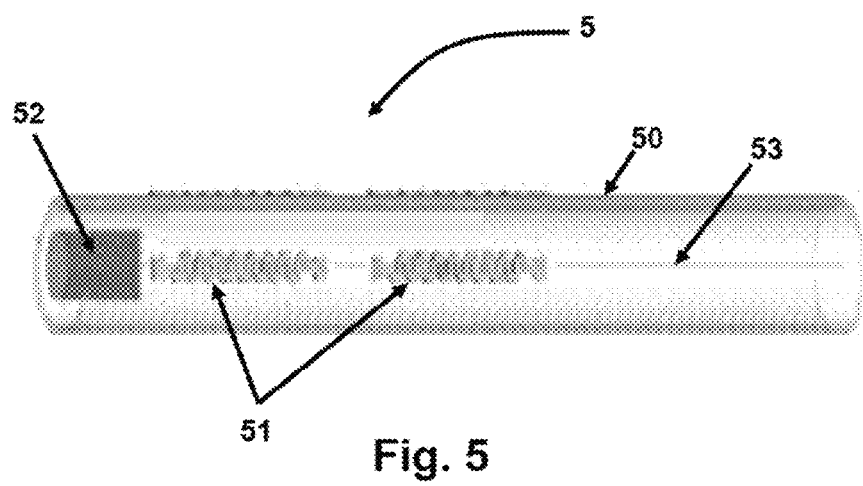
FIG. 5 is an illustrative diagram of a catheter including grafted polymers and Ti—Ni SMA actuators.

Catheters of other embodiments may incorporate different means for causing bending. For example, embodiments include catheters that incorporate microelectromechanical systems (MEMS), piezoelectric technology, shaped-memory alloys (SMA), and combinations thereof, as well as, the flexible substrates, grafted polymers, stimuli producing elements, and guide wires as discussed above. For example, embodiments include catheters 5 that include, for example, Ti—Ni SMA spring actuators 51 for catheter actuation, ultrasonic piezoelectric transducers 52 for forward-looking, guidewires 53, spiral wiring for various flexure motions, and a polyurethane tube catheter coating 50 as illustrated in FIG. 5. Bending can be accomplished by using Ti—Ni SMA spring actuators 51, guidewires 53, or spiral wiring.

In still other embodiments, electro-chemically activated electrodes can be incorporated into the catheters of the invention. For example, in one exemplary embodiment, a commercial catheter can be coated with polypyrrole (PPy)

that can be laser micromachined into electrochemically activatable electrodes. Stimuli producing elements may produce an electrochemical stimuli such as, oxidation an reduction leading to bending of the catheter. In other embodiments, a copper film can be deposited on a catheter by, for example, sputter coating, and this copper film can be patterned by a laser machining. PPy can then be polymerized on the copper film. Providing a charge to the copper film can then initiate bending of the catheter.

Figure 6:
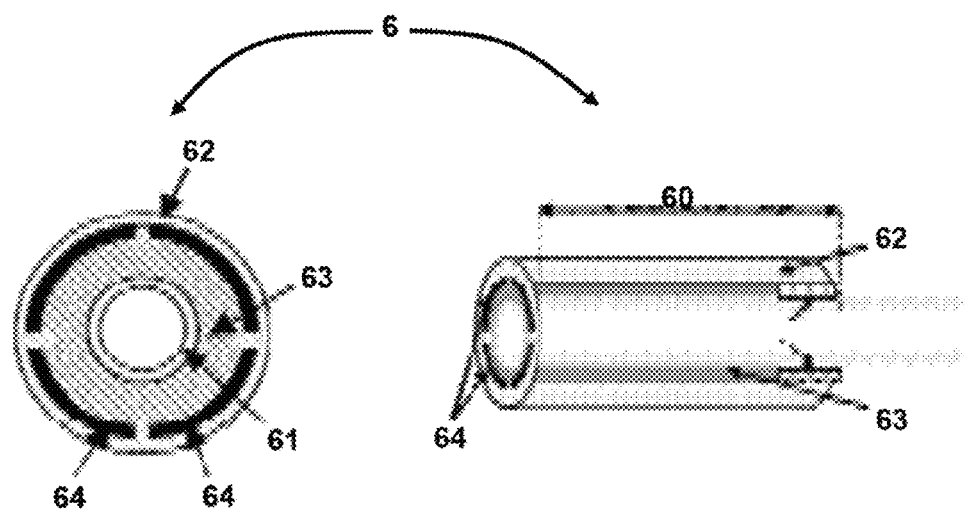
FIG. 6 is an illustrative diagram of a catheter having electrochemical actuation.

In still other embodiments, conducting polymer actuators may be incorporated into the catheters of the invention. For example, ionic polymer metal composites (IPMC), a type of artificial muscle actuator, can be incorporated into the catheters of embodiments to produce a steerable catheters. Since electrochemical actuation of these devices involves using ionic electrolytes, encapsulation is often required. As illustrated in FIG. 6, such catheters 6 may include a catheter tip 61 and catheter tube enclosed within an encapsulation tube 62 to create a secondary lumen that can be filled with an electrolyte solution 63. Polymer electrodes 64 may be disposed around an outer circumference of the encapsulation tube 62 and may stimulate bending.

In some embodiments, the devices including the grafted polymer brush layers described above may further include a means for force feedback. Any means known in the art for detecting contact or the force of a contact between the device and, for example, a blood vessel or determining the frictional force between the blood vessel walls and the catheter tube may be used in the devices described herein. For example, in some embodiments, micro-optical force sensors may be incorporated into the devices of the invention to provide force feedback, and in other embodiments, piezoelectric tactile sensors may be incorporated to provide force feedback.

Other embodiments are directed to a catheter tip including a section of a tube having sufficient length to allow for bending, and a conical or cone shaped end similar to the catheter ends tips currently available. The catheter tip of such embodiments may be prepared from any of the flexible substrate materials described above and may be coated on one or more inner or outer surfaces with a grafted polymer such as those described above over the entire surface or in one or more specific locations. The tip may further include one or more additional grafted elements such as those described above that are configured to provide stimuli to grafted polymer. In some embodiments, the catheter tip may be configured to attach to an existing catheter and provide a bendable tip.

Some embodiments are directed to a method for preparing a device including providing a device; and applying a macroscale grafted polymer brush to at least one portion of the device. In some embodiments, the device comprises a catheter. In some embodiments, the method further includes attaching a stimuli producing element to the device adjacent to the macroscale grafted polymer brush. In some embodiments, the method further includes connecting the stimuli producing element to a control module. In some embodiments, the at least one portion of the device comprises a flexible substrate. In some embodiments, the flexible substrate comprises a shore value of about 20 A to about 70 D, or about 40 A to about 100 A or any value between these ranges. Specific examples of shore values include about 20 A, about 30 A, about 40 A, about 50 A, about 60 A, about 70 A, about 80 A, about 90 A, about 100 A, and ranges between these values.

In some embodiments, the flexible substrate comprises thermoplastic elastomers (TPE) or other elastomers such as, for example, polyester ethers, copolyester ethers such as ECDEL, styrene based TPE, olefin based TPE, urethane based TPE, ester based TPE, amide based TPE, polyolefins, natural rubber, synthetic rubber, poly (acrylates/methacrylates), hydrogels (synthetic and natural), and silicone rubbers. In some embodiments, the flexible substrate comprises a surface comprising functional groups such as sulfur-containing functional groups such as thiols, sulfides, disulfides (e.g., —SR or —SSR where R is alkyl, typically lower alkyl, or aryl), and the like; tri-substituted silanes —$SiX_3$ where X is halo or lower alkoxy (typically chloro or methoxy); carboxylic acids; hydroxamic acids; acid chlorides; anhydrides; epoxides; peroxide groups; nitrile groups; thioester groups; alkoxamine groups; ester groups; haloester groups; sulfonyl groups; phosphoryl groups; hydroxyl groups; amino acid groups; amides; and the like and combinations of these. In some embodiments, the grafted polymer brush comprises PEG-based monomers such as poly (ethylene glycol) methyl ether acrylate, poly(ethylene glycol) methyl ether methacrylate, poly(ethylene glycol) methyl ether acrylamide, poly(ethylene glycol) methyl ether methacrylamide, poly(vinyl methyl ether), poly(N-vinyl caprolactam), poly(N,N-dimethylacrylamide), poly(N-2,3-dihydroxylpropyl)acrylamide, poly(2,2-dimethyl-1,3-dioxalane)methyl] acrylamide, polydodecyl methacylate (PDMA), dodecyl methacrylate (DMA), poly-n-butyl acrylate (PnBA), styreneacrylonitrile copolymer (AS), polypropylene-polymethyl methacrylate (PMMA), neutral hydrophilic monomers such as acrylamide, N-acryloylmorpholine, 2-hydroxyethyl methacrylate (HEMA), N-isopropylacrylamide (NIPAM), 2-methoxyethyl acrylate (MEA), 2-methacryroyloxyethylphosphorylcholine (MPC), acrylamide/methacrylamide derivatives of carbohydrates, [3-(Methacryloylamino) propyl]dimethyl(3-sulfopropyl)ammonium hydroxide (SBMA), 1-vinyl-2-pyrrolidone (VP), basic monomers such (3-acrylamidopropyl) trimethylammonium (APTA), allylamine (AA), 1,4-diaminobutane methacrylamide (DABMA), acidic such as 2-acrylamido-2-methyl-1-propanesulfonic acid (AMPS), ethylene glycol methacrylate phosphate (EGMP), hydrophobic monomer such as 2,2,2-trifluoroethyl methacrylate (TFEM), light sensitive polymer such as azobenzene containing copolymers of poly(ethyleneglycol) methacrylate, temperature sensitive polymers of N-substituted acrylamides/methacrylamides (PAM) and various combinations of these.

Some embodiments herein are directed to a kit including a device comprising a macroscale grafted polymer brush coating on at least one surface of a flexible substrate; and instructions on how to use the device. In some embodiments, the device is a catheter. In some embodiments, the device may be any device described herein. In some embodiments, the flexible substrate comprises thermoplastic elastomers (TPE) or other elastomers such as, for example, polyester ethers, copolyester ethers such as ECDEL, styrene based TPE, olefin based TPE, urethane based TPE, ester based TPE, amide based TPE, polyolefins, natural rubber, synthetic rubber, poly (acrylates/methacrylates), hydrogels (synthetic and natural), and silicone rubbers. In some embodiments, the flexible substrate comprises a surface comprising functional groups such as sulfur-containing functional groups such as thiols, sulfides, disulfides (e.g., —SR or —SSR where R is alkyl, typically lower alkyl, or aryl), and the like; tri-substituted silanes —$SiX_3$ where X is halo or lower alkoxy (typically chloro or methoxy); carboxylic acids; hydroxamic acids; acid chlorides; anhydrides; epoxides; peroxide groups; nitrile groups; thioester groups;

alkoxamine groups; ester groups; haloester groups; sulfonyl groups; phosphoryl groups; hydroxyl groups; amino acid groups; amides; and the like and combinations of these. In some embodiments, the grafted polymer brush comprises PEG-based monomers such as poly(ethylene glycol) methyl ether acrylate, poly(ethylene glycol) methyl ether methacrylate, poly(ethylene glycol) methyl ether acrylamide, poly(ethylene glycol) methyl ether methacrylamide, poly(vinyl methyl ether), poly(N-vinyl caprolactam), poly(N,N-dimethylacrylamide), poly(N-2,3-dihydroxylpropyl)acrylamide, poly(2,2-dimethyl-1,3-dioxalane)methyl] acrylamide, polydodecyl methacylate (PDMA), dodecyl methacrylate (DMA), poly-n-butyl acrylate (PnBA), styrene/acrylonitrile copolymer (AS), polypropylene-polymethyl methacrylate (PMMA), neutral hydrophilic monomers such as acrylamide, N-acryloylmopholine, 2-hydroxyethyl methacrylate (HEMA), N-isopropylacrylamide (NIPAM), 2-methoxyethyl acrylate (MEA), 2-methacryroyloxyethylphosphorylcholine (MPC), acrylamide/methacrylamide derivatives of carbohydrates, [3-(Methacryloylamino) propyl]dimethyl(3-sulfopropyl)ammonium hydroxide (SBMA), 1-vinyl-2-pyrrolidone (VP), basic monomers such (3-acrylamidopropyl) trimethylammonium (APTA), allylamine (AA), 1,4-diaminobutane methacrylamide (DABMA), acidic such as 2-acrylamido-2-methyl-1-propanesulfonic acid (AMPS), ethylene glycol methacrylate phosphate (EGMP), hydrophobic monomer such as 2,2,2-trifluoroethyl methacrylate (TFEM), light sensitive polymer such as azobenzene containing copolymers of poly(ethyleneglycol) methacrylate, temperature sensitive polymers of N-substituted acrylamides/methacrylamides (PAM) and various combinations of these.

Some embodiments are directed to a kit including a flexible substrate comprising a stimuli producing element, wherein the tube is coated with a grafted polymer brush on at least one surface, and wherein the stimuli producing element is capable of allowing the flexible substrate to bend. In some embodiments, the flexible substrate comprises a tube having a lumen. In some embodiments, the lumen is capable of encompassing a catheter. In some embodiments, the lumen is capable of encompassing any device described herein. In some embodiments, the catheter is comprised of a flexible substrate material.

In some embodiments, the flexible substrate comprises polyester ethers, styrene based thermoplastic elastomers (TPE), olefin based thermoplastic elastomers (TPE), urethane based thermoplastic elastomers (TPE), ester based thermoplastic elastomers (TPE), amide based thermoplastic elastomers (TPE), polyolefins, copolyester ethers, silicone rubbers, or combinations thereof. In some embodiments, the flexible substrate comprises a surface comprising functional groups such as thiols, sulfides, disulfides, tri-substituted silanes, carboxylic acids, hydroxamic acids, acid chlorides, anhydrides, epoxides, sulfonyl groups, phosphoryl groups, hydroxyl groups, amino acid groups, amides, or combinations thereof. In some embodiments, PEG-based monomers such as poly(ethylene glycol) methyl ether acrylate, poly(ethylene glycol) methyl ether methacrylate, poly(ethylene glycol) methyl ether acrylamide, poly(ethylene glycol) methyl ether methacrylamide, poly(vinyl methyl ether), poly(N-vinyl caprolactam), poly(N,N-dimethylacrylamide), poly(N-2,3-dihydroxylpropyl)acrylamide, poly(2,2-dimethyl-1,3-dioxalane)methyl] acrylamide, polydodecyl methacrylate (PDMA), dodecyl methacrylate (DMA), poly-n-butyl acrylate (PnBA), styreneacrylonitrile copolymer (AS), polypropylene-polymethyl methacrylate (PMMA), neutral hydrophilic monomers such as acrylamide, N-acryloylmorpholine, 2-hydroxyethyl methacrylate (HEMA), N-isopropylacrylamide (NIPAM), 2-methoxyethyl acrylate (MEA), 2-methacryroyloxyethylphospsporylcholine (MPC), acrylamide/methacrylamide derivatives of carbohydrates, [3-(Methacryloylamino) propyl]dimethyl(3-sulfopropyl)ammonium hydroxide (SBMA), 1-vinyl-2-pyrrolidone (VP), basic monomers such as (3-acrylamidopropyl)trimethylammonium (APTA), allylamine (AA), 1,4-diaminobutane methacrylamide (DABMA), acidic such as 2-acrylamido-2-methyl-1-propanesulfonic acid (AMPS), ethylene glycol methacrylate phosphate (EGMP), hydrophobic monomer such as 2,2,2-trifluoroethyl methacrylate (TFEM), light sensitive polymer such as azobenzene containing copolymers of poly(ethyleneglycol) methacrylate, temperature sensitive polymers of N-substituted acrylamides/methacrylamides (PAM) and various combinations of these.

The devices of embodiments may further include additional components. For example, in various embodiments, the devices, such as catheters, may further include additional components such as stents positioned for delivery to a patient, therapeutic agents on a surface of the device or held within a container within the device, ablation apparatuses such as laser or sonic ablation devices, devices for detecting abnormalities including optical devices such as fiber optic cameras, interferometry devices, spectroscopy devices, and the like and combinations thereof. In further embodiments, the devices of the invention may include one or more control apparatuses. For example, in some embodiments, the device may include a control module that allows the user to provide stimuli to a portion of the device having a grafted brush polymer coating to induce bending of the device. In such embodiments, the control module may be incorporated into the device using, for example, wires or other connecting means, and in some embodiments, the control module may be a separate apparatus that is connected to the device using, for example, wires.

The control module may further control any additional components included in the device, or in some embodiments, individual control modules may be provided to control the additional components. The control modules themselves may be configured to control the device and/or additional components using any means such as, for example, dials, buttons, or joysticks. In certain embodiments, the control modules of embodiments may include one or more video screens for displaying video or visualizing data retrieved from the device or additional components incorporated into the devices of embodiments. The one or more video screens may be incorporated into the control device or may be separate devices that are connected to the control apparatus. The control modules may be connected to the devices of various embodiments using any means and the connections may be permanent or reversible. For example, in some embodiments, reversible connectors may allow the control modules to be disconnected from the device allowing a single control module to be used with a number of devices.

Still further embodiments are directed to methods for using the devices of the invention. In some embodiments, such methods may include introducing a catheter having one or more portions that is coated with a grafted polymer brush into a vessel of a patient and applying stimuli to the one or more portions of the catheter coated with the grafted polymer brush, wherein the stimuli induces bending of the catheter at the portions of the catheter having the grafted polymer brush coating. The stimuli may induce bending by causing the individual components (bristles) of the grafted polymer brush coating to become attracted to one another causing the portion of the catheter having the grafted polymer coating to contract or cause the individual components (bristles) of the grafted polymer brush coating to repel one another causing the portion of the catheter having the grafted polymer coating to stretch. In still other embodiments, opposing surfaces of the portion of the catheter may be coated with the grafted polymer brush, and applying stimuli may result in concerted contracting and stretching of the grafted polymer brush coatings on the opposing surfaces. Other embodiments may include removing the stimuli thereby reducing or relieving the bending and allowing the catheter to retain its straight configuration.

In still other embodiments, methods encompassed by the invention delivering therapy to the patient using the catheters described above having at least one surface coated with a grafted polymer brush, and certain embodiments are directed to methods for detecting abnormalities in the vessel of a patient using the catheters of various embodiments. Such embodiments are not limited to a particular form of therapy. For example, in various embodiments, the catheter may deliver stents, therapeutic agents, ablation apparatuses such as laser or sonic ablation devices, and the like or combinations thereof, and any device known and used in the medical arts for detecting abnormalities may be used to detect abnormalities such as, for example, optical devices such as fiber optic cameras, interferometry devices, spectroscopy devices, and the like, and combinations thereof. In further embodiments, technologies used for detection and delivering therapy may be provided in the same catheter. For example, a catheter embodied by the invention may include a detection apparatus, such as a fiber optic camera, and a therapy delivering device, such as an ablation apparatus. Thus, methods for using the catheters of the invention may include the steps of introducing a catheter having at least one surface coated with a grafted polymer brush into a vessel of a patient, applying stimuli to the one or more portions of the catheter coated with the grafted polymer brush to induce bending of the catheter at the portions of the catheter having the grafted polymer brush coating, detecting an abnormality in the vessel of the patient, and/or delivering a therapy to the patient at the abnormality.

Still further embodiments are directed to methods for making the devices of the invention. Such embodiments generally include the step of applying a grafted polymer brush to at least a portion of a device. In some embodiments, the device may be a medical device, and in certain embodiments, the device may be a catheter. As discussed above, the catheter may be of any commonly used diameter (3 Fr to 34 Fr). The grafted polymer brush may be applied to any portion of the device, and in some embodiments, the grafted polymer brush may be applied to more than one portion of the device. In certain embodiments, the grafted polymer may be applied to the device tip, within about 1 mm to about 10 cm from the distal most end of the device, and in other embodiments, the grafted polymer may be applied at the device tip and at a portion of the device away from the distal most end of the device. For example, in some embodiments, methods for preparing a device may include applying a grafted polymer brush at the distal most end of the device, and other embodiments may include the step of applying the grafted polymer brush to the distal most end of the device and applying the grafted polymer brush to a portion of the device proximal to the distal most end of the device.

The devices of embodiments described above may be prepared by any method known in the art. For example, in some embodiments, a coating of a grafted polymer may be applied to a substrate such as a catheter tube using 2,2'-azobis(2-methylpropionitrile) (azobisisobutyronitrile or AIBN), AIBN-initiated free-radical polymerization, peroxide-initiated free-radical polymerization, atom transfer radical polymerization (ATRP), nitroxide mediated polymerization, cationic polymerization, anionic polymerization, condensation polymerization or reversible addition-fragmentation chain transfer (RAFT) polymerization or a combinations thereof. Thus, various embodiments are directed to methods for preparing the devices described herein using these polymerization methods.

The methods for making such devices may further include providing a stimuli producing element to the grafted polymer brush coating. Stimuli producing elements are described above, and embodiments for making the devices of the invention include providing a type of stimuli producing element described herein. For example, in some embodiments, methods for making a device of the invention may include the step of attaching a heat producing element to a surface of the device adjacent to the grafted polymer brush and connecting the heat producing element to a control module with, for example, a wire. The control module may be incorporated into the device or may be a separate module or apparatus connected to the device using, for example, wires or other connecting means.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number 11 (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense of one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense of one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," and the like include the number recited and refer to ranges which can be subsequently broken down into subranges, as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

EXAMPLES

Macroscale bending of pPVC film was performed as a proof-of-concept using single side surface initiated-atom transfer radical polymerization (SI-ATRP) initiator modified pPVC substrate having no noticeable initial curvature.

Example 1—Preparation of Coated Substrates

The coated substrate was prepared as follows:
Water-soluble and expoxide-functionalized ATRP initiator wasp as shown in Scheme 1:

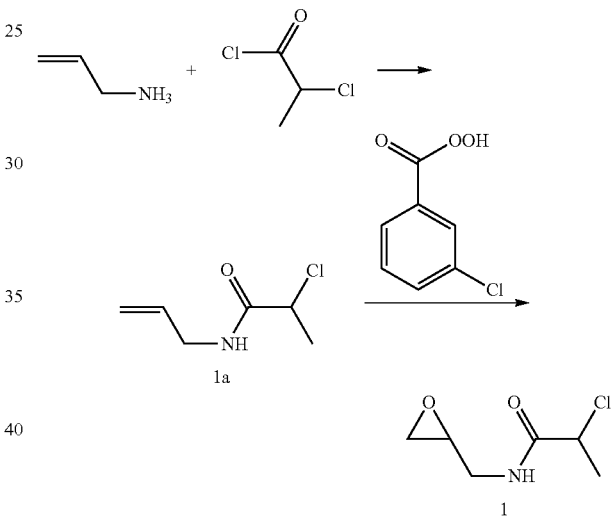

Allylamine (5 ml) was mixed with 60 ml of dichloromethane and triethylamine (1.1 molar equivalent) into a 100 ml round bottom flask. 2-Chloro-propionyl chloride (1 molar equivalent) was added dropwise to the solution with gentle stirring at 0° C., continued at room temperature for 16 h. The reaction mixture was filtered and washed with saturated sodium bicarbonate solution and water, followed by drying over sodium sulfate. After removing the solvent, the crude compound 1a was purified by column chromatography using hexane/ethyl acetate as eluent. The yield was c.a. 95%.

Figure 7:
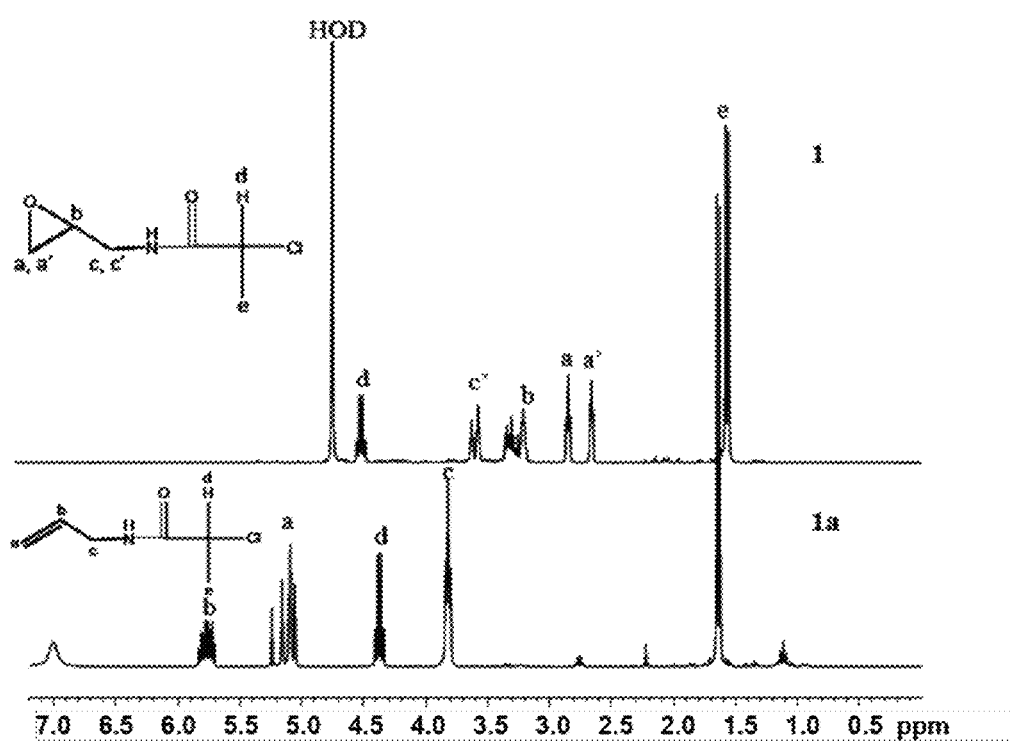
FIG. 7 is a representative $^1$H NMR spectrum of epoxide-functionalized water-miscible ATRP initiator 1.

Compound 1a (6 g) was further oxidized in DCM (150 ml) using metachloroperoxybenzoic acid (m-CPBA, 2 molar equivalent) for 48 h. The reaction mixture was filtered, washed with saturated sodium bisulfite to remove the excess m-CPBA, and finally washed with sodium bicarbonate and water. The organic layer was dried over sodium sulfate. After removing the solvent, the crude compound was purified by column chromatography using hexane/ethyl acetate as eluent. The typical yield of the epoxide-functionalized ATRP initiator 1 was c.a. 45%. The pure compound 1 was miscible with water at c.a. 2% wt/v. $^1$H NMR of compounds 1a (in CDCl$_3$) and 1 (in D$_2$O) are provided in FIG. 7.

Plasticized poly(vinyl chloride) (pPVC) is a versatile polymeric material used extensively in various biomedical applications including platelet and blood storage bags, tubing for extracorporeal circulation, and intravenous catheters. Modification of pPVC has rarely been reported, especially using SI-ATRP strategy. Although organic solvents such as toluene, THF, and DMF are commonly used for SI-ATRP when inert substrates such as silicon wafer or graphene are used many polymeric substrates including plasticized PVC are not compatible with organic solvents due to the dissolution or leaching of plasticizer. Therefore, to minimize the impact of organic solvents on the pPVC substrate, all surface modifications and surface-initiated polymerizations employed in the current study were designed to proceed in aqueous conditions or by mild plasma treatment.

Figure 8:
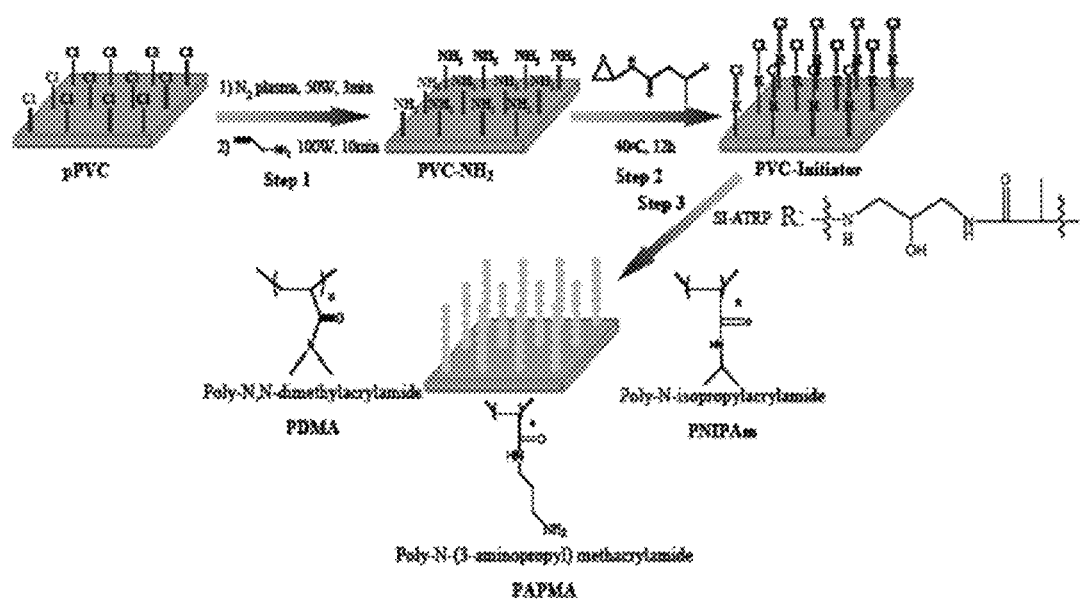
FIG. 8 is a schematic illustration of surface modification of pPVC—step 1: surface amination via allylamine plasma treatment; step 2: coupling of ATRP initiator; step 3: surface initiated ATRP of DMA, NIPAm, and APMA from pPVC.

Surface grafting of hydrophilic polymers on pPVC was carried out via three steps as shown in FIG. 8. The initiator-modified pPVC with thickness of 400 μm was pre-cut into samples having 1.5 cm-0.25 cm dimensions, cleaned with water, and completely dried under vacuum at ambient temperature. In Step 1, plasma treatment was performed on M4L RF plasma system (PVA Tepla, U.S.) to introduce amino groups on to the pPVC samples. More specifically, pPVC was pre-activated by nitrogen plasma for three minutes at watts, followed by treatment of allylamine plasma for ten minutes at 100 watts. Pretreatment of the substrate by inert gas plasma such as nitrogen, argon, and oxygen can clean and pre-activate the substrate, and subsequently improve the efficiency of the final plasma treatment. Nitrogen plasma was selected to pre-treat pPVC surface due to the higher surface amine content obtained compared to argon and oxygen plasma. Allylamine plasma has been widely applied for surface amination due to the generation of high concentration of amine groups obtained (5-12 per $nm^2$), which is a very important prerequisite for obtaining polymer brushes with high grafted density. The treated pPVC sample was transferred into a 1 L beaker filled with DI water and sonicated for 30 minutes. The aminated pPVC (PVC-$NH_2$) showed significantly lower water contact angle (~55°) compared to untreated pPVC (~90°). In the case of single-side treatment, pPVC sample was blocked by aluminum foil on one side with a tape sealing on the edges. In the case of both-side treatment, a pPVC sample was suspended in the chamber of the plasma generator to provide a uniform treatment on both sides.

Figure 9D:
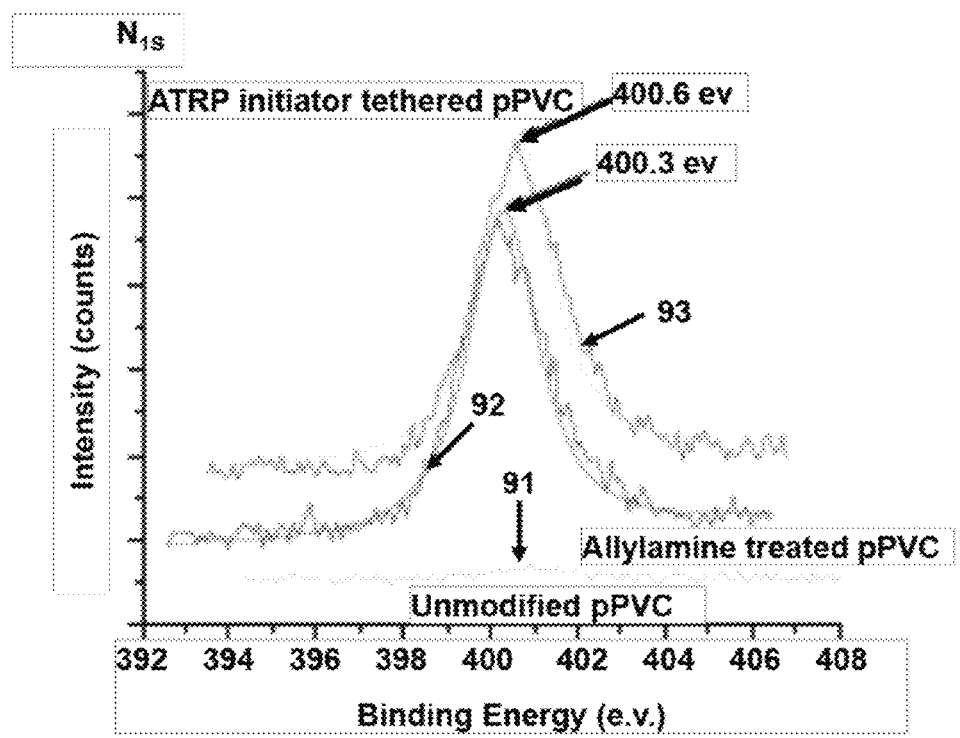
FIG. 9D depicts detailed $N_{1S}$ scans of untreated (91), allylamine treated (92), and ATRP initiator tethered pPVC (93) surfaces. There was no $N_{1S}$ peak observed for unmodified pPVC. $N_{1S}$ peak for allylamine treated pPVC surface and ATRP initiator tethered pPVC surface was observed at 400.3 and 400.6 e.v., respectively.

Comparison of the treated and untreated pPVC was highlighted in FIG. 9A-C. pPVC sample covered by a flat stainless steel mesh with regularly aligned round holes was treated with allylamine plasma. After sonication, the sample was removed from the water and a photo was taken, FIG. 9A. Due to the blocking effect of the cover, only the exposed area was aminated. As shown in FIG. 9A, the water droplet selectively aggregated on the aminated area due to its hydrophilicity. X-ray photoelectron spectroscopy (XPS) results further verified the presence of nitrogen (N) on the treated area, FIG. 9B, in contrast to untreated area. FIG. 9C. A further detailed scan of nitrogen binding energy for unmodified, allylamine treated, and ATRP initiator tethered pPVC surface revealed that amine groups were predominant on the allylamine treated pPVC surface (B.E. 400.3 e.v.), FIG. 9D, while no nitrogen was observed on unmodified pPVC surface. After ring opening reaction, the binding energy of $N^{1S}$ on ATRP initiator tethered surface shifted to 400.6 e.v., which confirmed the successful conversion of —$NH_2$ and —NH—C— functionality to tertiary amine.

In Step 2 of FIG. 8, the aminated pPVC sample was reacted with epoxide-functionalized ATRP initiator (1% wt/v) in aqueous condition at 40° C. for 12 h. ATRP initiators incorporated through ring-opening reaction of primary and secondary amine groups with epoxide containing ATRP initiators. The pPVC tethered with ATRP initiator obtained was then sonicated in water for 30 minutes to remove the adsorbed free ATRP initiator and was stored in water before use.

In Step 3 of FIG. 8, ATRP polymerization was carried out to provide the graft polymer brush. All ATRP polymerizations were carried out in a glove box filled with argon at room temperature. Water was degassed with argon for 1 h before use. In a typical reaction set-up, copper (I) chloride (Cu(I)Cl) (5 mg) and 1,1,4,7,10,10-hexamethyltriethylenetetramine (HMTETA) (40 mg) were added to 20 mL of a 10 wt. % dimethylacetamide solution (DMA/$H_2O$) into a sample vial, and this mixture was mixed well. ATRP initiator-tethered pPVC specimens were cut into the desired size, placed into sample vials, and swirled gently. The reaction proceeded at ambient temperature (22° C.) for a given period of time after which pPVC samples were washed thoroughly with water and sonicated for 30 min prior to being stored in water. The molecular weight and grafted density were modulated by changing monomer concentration and polymerization time. pPVC is used as a flexible substrate. Poly(N,N-dimethylacrylamide), hydrophilic polymer, is used as an example of neutral polymer. Poly(N-isopropylacrylamide) is used as an example of hydrophilic temperature responsive polymer, and poly-N-(3-aminopropyl)methacrylamide is used as an example of pH responsive polymer.

Example 2—Characterization of Grafted Polymers

The molecular weight of the grafted polymers was estimated from the solution polymers formed along with SI-ATRP. FIG. 10A shows representative GPC profiles of three PDMA samples, which were formed during SI-ATRP in 2%, 5%, and 10% of DM concentration (wt %). The grafting density of the PDMA brushes grown for 2 h, 6 h, 12 h, and 24 h determined. These values were obtained by measuring the dry weight of the PDMA grafted pPVC surface, the molecular weight of the chains formed in solution, and the area of pPVC samples used. The grafted density values for 12 h and 24 h SI-ATRP were 1.12 and 1.65 chains/nm, respectively. An increase in grafted density with polymerization time was observed.

Structures of the surface grafted polymers were characterized by ATR-FTIR. As an example, FIG. 10B shows ATR-FTIR spectrum of unmodified pPVC and PDMA-grafted pPVC. With increase in the DMA monomer concentration, the peak intensity representing amide I gradually increased suggesting the increased amount of grafted PDMA. In contrast, the absorbance belonging to plasticizer at 1735 $cm^{-1}$ gradually decreased, presumably due to the blocking effect of the grafted PDMA layer.

Figure 11E:
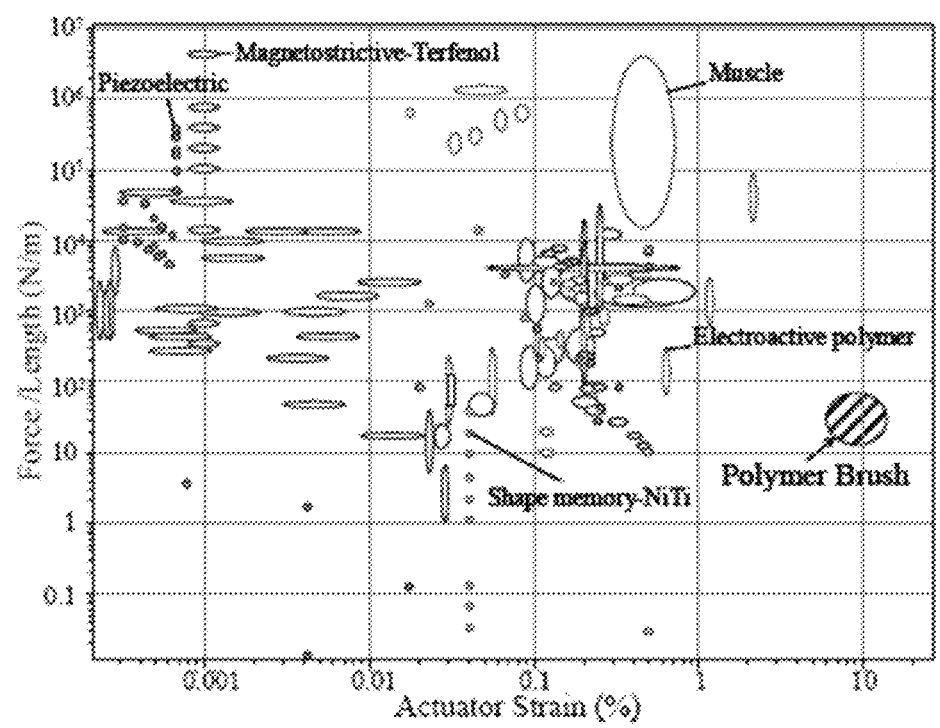
FIG. 11E is a chart depicting a comparison of polymer brush actuator with other available actuators based on two performance indices: force per unit length and actuator strain.

Keeping the bulk properties of pPVC intact during the surface modification is ideal for applications such as those embodied by the invention. Therefore, tensile strength of pPVC before and after surface modification was compared. Tensile testing of the samples was done at 22±1° C. according to the ASTM D 412-80 test method using dumb-bell shaped test specimens in an Instron Universal Testing Machine (model 1195) at a cross-head speed of 500 mm/min. As shown in FIG. 11A, PDMA-grafted pPVC (10% DMA concentration) shows similar force displacement curve compared to unmodified pPVC. Therefore, the observed bending and stretching can be solely attributed to the surface-grafted polymers, instead of the change of bulk properties of pPVC. FIG. 11B illustrates representative TGA curves of pPVC and PDMA-grafted pPVC (10% DMA, 24 h polymerization). Thermogravimetric analysis of PDMA grafted pPVC showed almost identical profiles as that of pPVC, suggesting the minimum influence of surface modification on the bulk properties of pPVC. Therefore, the observed bending and stretching can be solely attributed to the surface-grafted polymers, instead of the change of bulk properties of pPVC.

Figure 12:
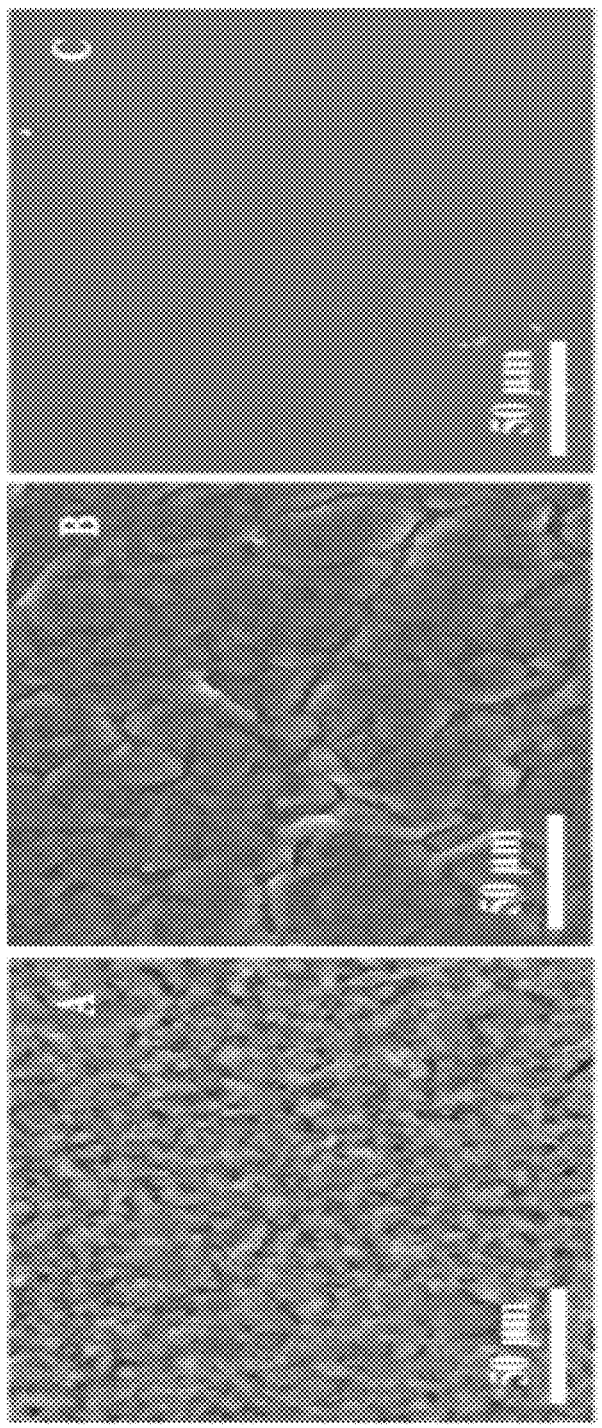
FIG. 12 are representative SEMs showing the topography of A) a blank pPVC surface; B) a PDMA-grafted pPVC surface (24 h polymerization), and C) a spin-coated PDMA/pPVC surface.
Figure 13:
FIG. 13 are representative cross-sectional BSE-SEM images of showing the topography of A) unmodified pPVC, B) pPVC grafted with PDMA (24 h SI-ATRP), and C) spin-coated PDMA on pPVC. The scale bars represent 5 µm.

Surface morphologies of unmodified pPVC, PDMA-grafted pPVC substrate (24 h SI-ATRP), and pPVC spin-coated with PDMA were compared by scanning electron microscopy (SEM). FIG. 12 shows SEM topography of three specimens. The difference reflects the different nature of two coatings. The topography of pPVC, A, and PDMA-grafted pPVC substrate, B, are relatively rougher compared to the spin-coated PDMA, C. Cross-sectional images of the samples are shown in FIG. 13. A sparsely spaced interface filled with vertically aligned fiber-like structures was observed for PDMA-grafted pPVC (FIG. 12B and FIG. 13B). In contrast, unmodified PVC and spin-coated PDMA did not show any special interfacial features (FIGS. 12A and 12C and FIGS. 13A and 13C). The thickness of the PDMA grafted layer on the pPVC was approximately 5 µm as measured from SEM images (approximately 1% of the thickness of pPVC substrate), correlating well to the ultra-high molecular weight of the PDMA chains.

Figure 18A:
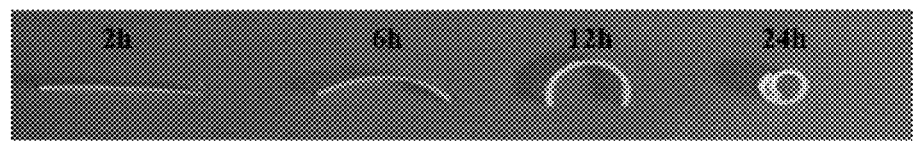
FIG. 18A are representative photographs showing the effect of polymerization time on bending of plasticized PVC substrate.
Figure 18B:
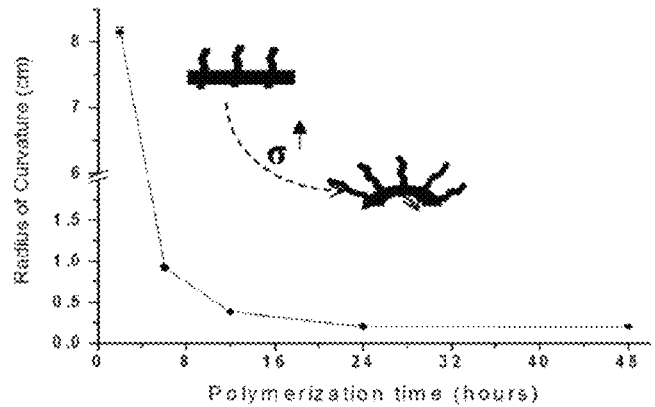
FIG. 18B is a graph showing the effect of polymerization time on bending.
Figure 18C:
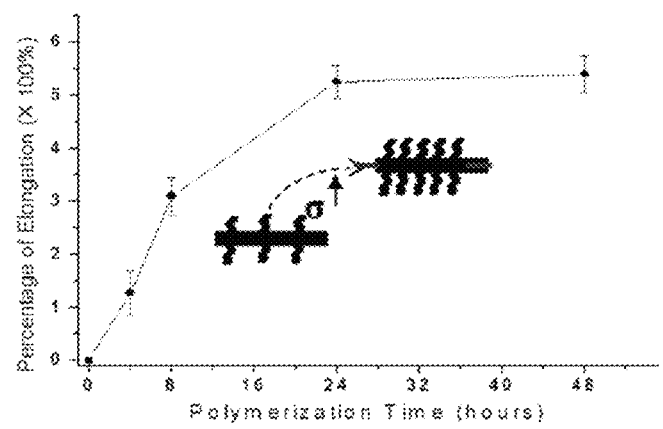
FIG. 18C is a graph showing the effect of polymerization on stretching deformation.

As shown in FIG. 18, the pPVC substrates were deformed with increase in the polymerization time. All pPVC substrates curved to the direction opposite to which the PDMA chains were grafted (FIG. 18A), and longer polymerization times resulted in gradual decrease in the radius of the curvature (FIG. 18B) and increase in elongation (FIG. 18C) of the substrates. Molecular weight of the PDMA chains formed in solution along with surface grafted chains remained constant after 2 h (Mn and Mw/Mn values were $1.5 \times 10^6$, $1.8 \times 10^6$, $2.1 \times 10^6$, $2.0 \times 10^6$ and 1.68, 1.75, 1.87, 2.00, respectively for 2, 6, 12, 24 h SI-ATRP), suggesting that the increase in bending deformation can be attributed to the increase in grafted density of polymer chains (i.e. increase in chain-chain repulsion) on the surface. Although the direct measurement of molecular weight may be desirable, Mn of the grafted PDMA chains were estimated from the solution polymers due to the incomplete cleavage of the amide linkage between the polymer and surface. Presence of amide bonds in the PDMA also complicated the cleavage process. The gradual increase in PDMA grafted density and the ultra high molecular weight of the chains are consistent with our previous observation of SI-ATRP of DMA from unplasticized PVC in aqueous solution.

Example 3—Characterization of Bending

Figure 19A:
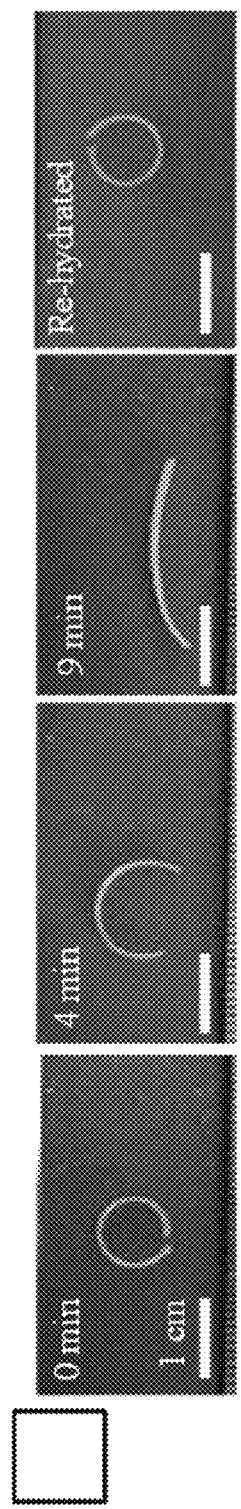
FIG. 19A are representative photographs showing the effect of dehydration-rehydration on the bending of a pPVC substrate grafted with PDMA chains on one side (12 h SI-ATRP).

A high degree of reversibility is essential for an ideal actuator design. FIG. 19A illustrates the effect of dehydration-rehydration by providing photographs of bending-flattening of single sided PDMA grafted pPVC substrate (12 h SI-ATRP) under atmospheric condition. Bending was observed when the single sided PDMA grafted pPVC substrate was wetted. FIG. 19A, first panel. At 45% relative humidity and 22° C., the PDMA grafted pPVC gradually dehydrated accompanied with flattening and finally reached an equilibrium state after 9 minutes, FIG. 19A, third panel. The dry sample reversed to its original bent shape upon rehydration within eight seconds, FIG. 19A, last panel. As illustrated in FIG. 19D, flattening and bending of the PDMA brush grafted pPVC is due to the conformational change of PDMA chains on the surface during the drying-wetting process. The hydrated chain dimensions of grafted PDMA decreased during the drying process resulted in reduced chain-chain interactions. During the rehydration, the polymer chains regains their original hydrated dimensions and the substrate reverts to its original shape. A control non-treated pPVC substrate did not show noticeable shape change during the wetting-drying process.

Figure 19B:
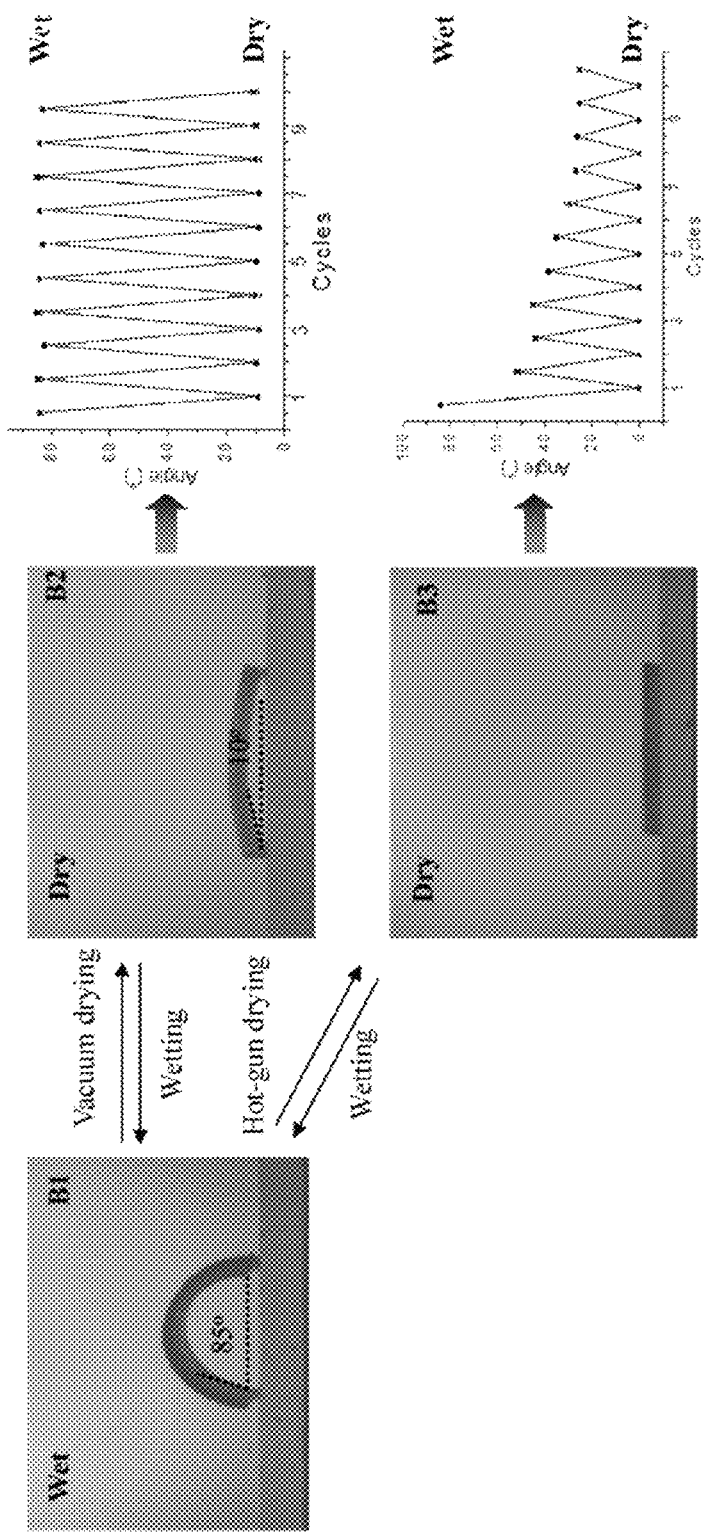
FIG. 19B includes representative photographs depicting the wet PDMA-grafted pPVC substrate, left panel, and the effect of vacuum drying, top panels, and hot gun drying, bottom panels, on the reversibility of the bending, and graphs showing the bending angles over time as the result of wetting-drying cycles under vacuum drying, top, and wetting-drying cycles under hot gun drying.
Figure 19C:
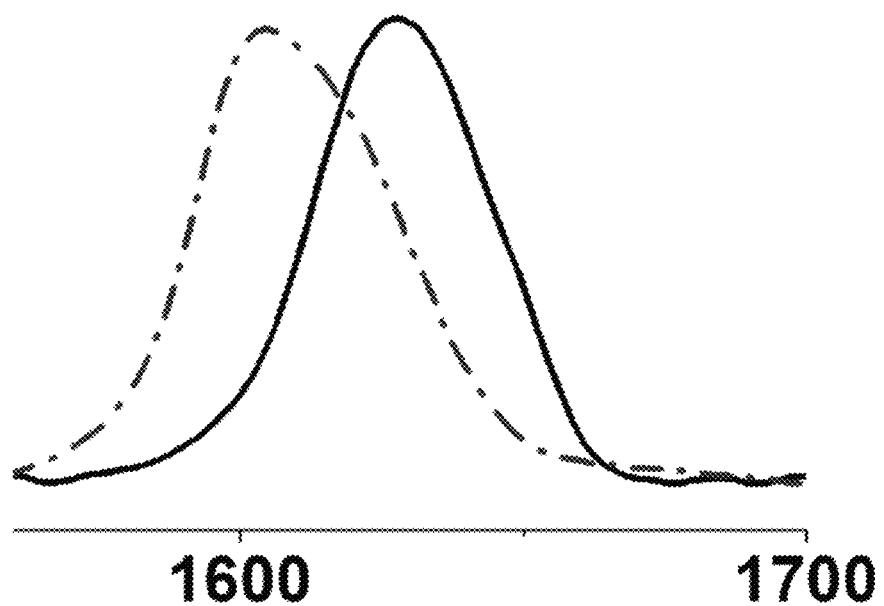
FIG. 19C is a graph showing the ATR-FTIR spectra of PDMA brush grafted pPVC substrate dried in vacuum (dotted curve) and hot gun (solid line).

To obtain quantitative information on the reversibility of bending-flattening process, a wet PDMA grafted pPVC substrate was dried by two approaches: vacuum drying (22° C. 0.1 Pa, 15 min) and hot-gun drying (180° C., 10 seconds). As shown in FIG. 19B, vacuum drying afforded a highly reversible bending-flattening process indicated by the minimal variation in the bending angles during the repeated process (FIG. 19B, upper right panel). In contrast, hot-gun drying (complete drying) led to a gradual decrease in bending angle (FIG. 19B, lower right panel) with repeated wetting-drying cycles, suggesting a more pronounced initial irreversibility. ATRFT-IR spectrum reveals that the water peak ($3400 \text{ cm}^{-1}$) observed for the vacuum dried substrate disappeared after hot-gun drying (FIG. 19C). The differences in the behavior of substrate subjected to two drying methods reflect the importance of the residual water on the reversibility of the bending-flattening process. The possible reason for the irreversible deformation in the case of hot-gun drying could be attributed to the polymer chain entanglement; the residual water in the specimen after vacuum drying might have prevented such entanglement resulting in high reversibility of the process.

To verify that the covalently grafted PDMA chains are responsible for the bending, we compared the bending-flattening process with a pPVC substrate spin-coated with PDMA on one side. The Mn of spin-coated PDMA was comparable to that of grafted chains and the dry thickness of the coating was c.a. 31 µm. There was no bending observed for spin-coated sample in the hydrated state, and it bended slightly to the PDMA coating side upon drying, which is presumably due to the contraction of the PDMA layer upon drying.

Figure 14A:
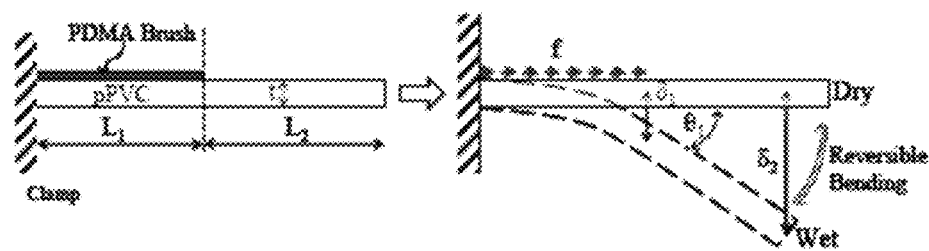
FIG. 14A is an illustrative engineering model that describes the bending behavior of PDMA-grafted on one side of pPVC substrate. The length of coated and uncoated segment was denoted as L1 and L2, respectively.

To understand the experimental observations further and to illustrate the application of this shape-memory mechanism for the generation of bending and stretching actuating devices (FIGS. 11, 14, and 17), we applied engineering principles. An engineering analysis of the experimentally observed bending deformations has been performed using beam theory. The polymer brush layer grafted onto the surface is assumed to exert an in-plane membrane force, f per unit width, at the polymer brush-substrate interface, in the plane of the interface as shown in FIG. 14A. This allows two deformations. In the first case, the substrate bends when either the upper or the lower surface alone is coated. This bending is similar to Stoney's observation of bending of nickel-plated metal strips due to residual stresses. In the second case, the substrate stretches when the same polymer brush structure is present on both sides (FIG. 3B). Consequently, both stretching and bending actuation of the substrate is possible with the polymer brush coatings. Based on the engineering analysis of the deformations, we estimate a membrane force of 24 N/m for 4 h polymerization time and Mn of $1.6 \times 10^6$ for bending actuators (FIG. 8). For the stretching case, the estimated force per unit length (FPL) for the upper and lower surfaces was 18.3 N/m and 12.9 N/m respectively.

When the polymerization time was increased from 4 hours to 24 hours, much higher values of 74.7 N/m and 67.3 N/m were deduced for the upper and lower surface, respectively (FIG. 14). This may be attributed to the increase in grafted density with increase in polymerization time. Elastic modulus of the pPVC did not change significantly after grafting PDMA chains on the surface.

It is instructive to compare polymer brush actuator with other existing actuators based on two mechanical indices for actuator performance: FPL and actuator strain. The actuator force per unit length is deduced from the engineering analysis. Actuator strain is the maximum strain the actuator undergoes. The FPL versus actuator strain diagram is shown in FIG. 7E wherein actuators drawn from an actuator database are compared with polymer brush based actuators. It can be observed that there is a trade-off between FPL and actuator strain, in general, for all actuators. Actuators with high FPL, such as piezoelectric materials, cannot provide large strains. Shape-memory metals such as Ni—Ti are attractive due to their larger strains. The polymer brush based actuators developed in this study are shown to provide even higher actuator strain (typically 10%) and moderate force per unit length: slightly better than some electro-active polymers. This comparison diagram underlines the potential for polymer brush actuators in material systems. We note that grafted density and molecular weight govern the FPL and actuator strain and the data reported here is for the experiments we conducted.

Figure 20:
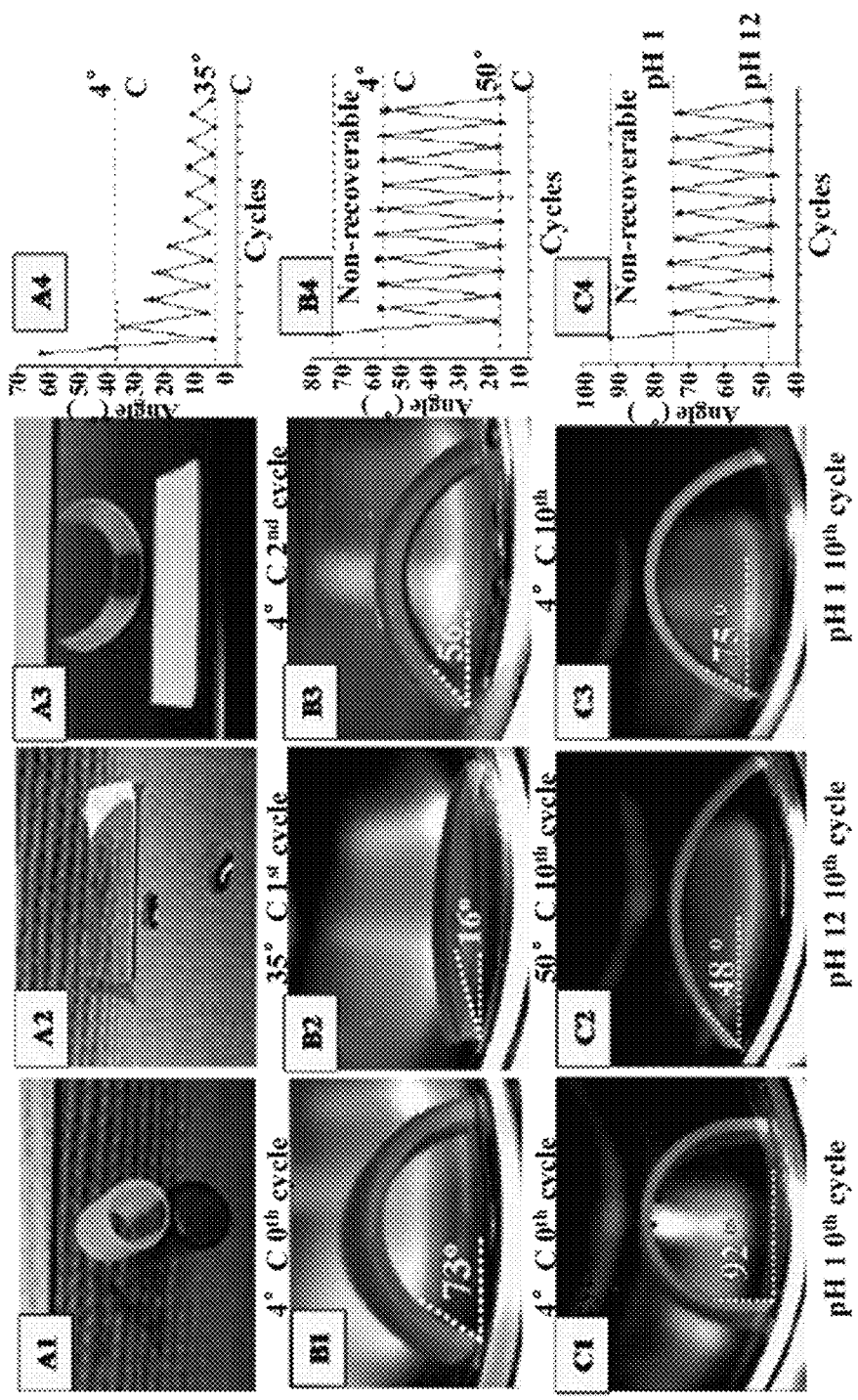
FIG. 20 depicts representative photographs of the polymer brush coated pPVC substrates subjected to different bending-flattening processes and conditions: A1-4 is PNIPAm; B1-4 is PNIPAm-co-PDMA; and C1-4 is PAPMA-co-PDMA.
Figure 21:
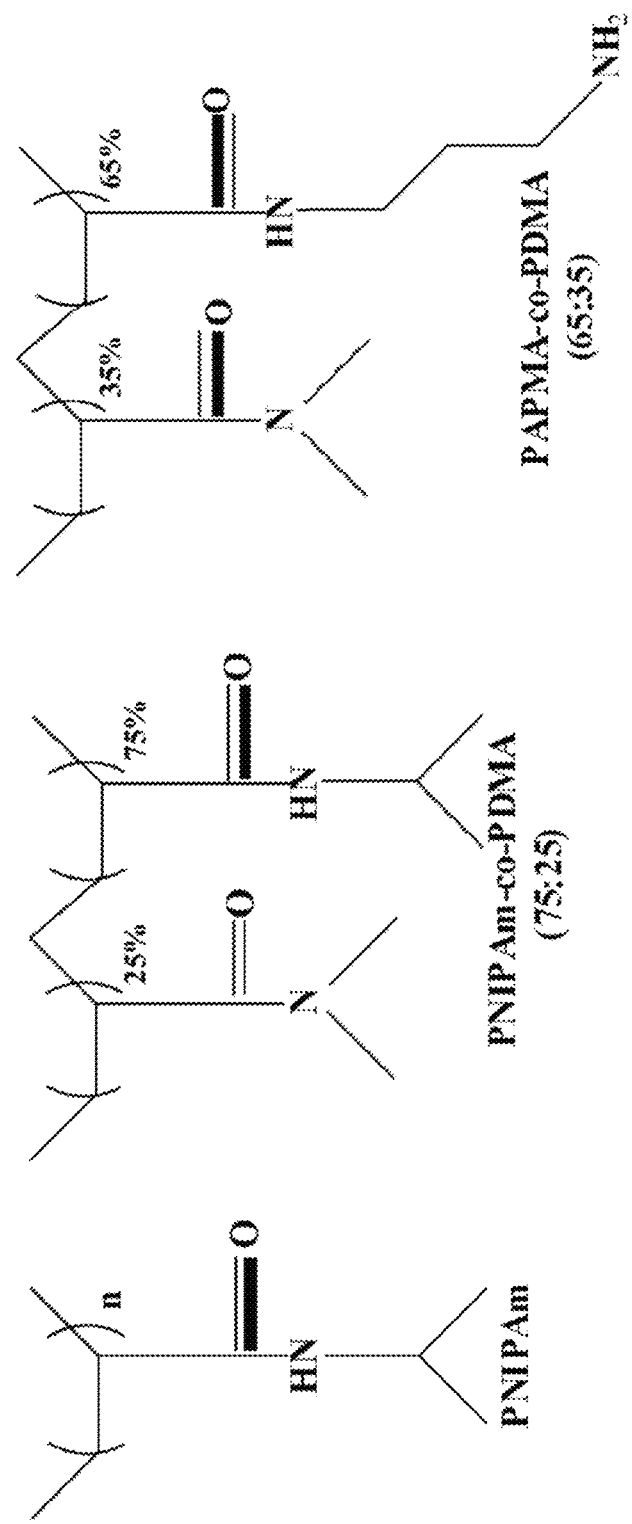
FIG. 21 depicts the grafting of PNIPAm, PNIPAm-co-PDMA in a ratio of 75:25, and PAPMA-co-PDMA in a ratio of 65:35.

To explore the application of this shape-change phenomenon further, we used two other external stimuli, temperature, and pH. To generate SMMs and actuators sensitive to temperature, a classical temperature-sensitive polymer, poly (N-isopropylacrylamide) (PNIPAm) and its copolymer with PDMA were used. As shown in FIG. 20, when a PNIPAm-grafted pPVC substrate (stored at 4° C. after polymerization) was heated to 35° C. followed by cooling to 4° C., an irreversible bending-flattening process was observed. The phase transition of the grafted PNIPAm may have resulted in chain entanglement, which was not reversed upon cooling (FIG. 20, Box A3), similar to the complete drying of PDMA brush seen earlier (FIG. 18B).

To overcome this, a PNIPAm-co-PDMA (75:25) was used resulting in nearly reversible bending-flattening process with heating-cooling cycles (FIG. 20, Box B3) The value of the bending angle was lowered c.a. 25% during the first cycle and remained constant afterwards. The reversibility of the process may be due to the fact that the PDMA component remained hydrated during the collapse of copolymer chains with temperature. Similarly, the grafting of a pH-sensitive copolymer, PDMA-co-poly(aminopropylmethacrylamide) (PAPMA) resulted in a pH sensitive substrate (FIG. 20, Box C4). Again, the introduction of a neutral PDMA component in the copolymer significantly improved the reversibility of the process.

Example 4—Engineering Analysis of Mechanical Deformations

Figure 14B:
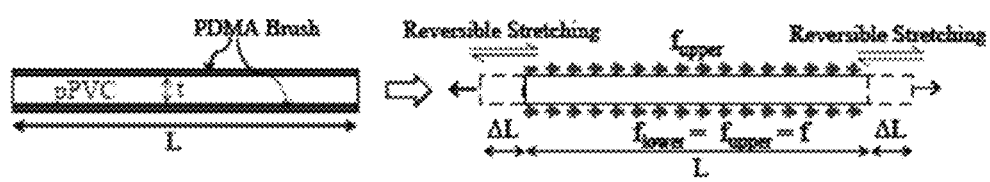
FIG. 14B is an illustrative engineering model predicting the stretching of pPVC with coating of PDMA on both sides.

The polymer brush layer is assumed to exert an in-plane membrane force, per unit width, at the brush-substrate interface, in the plane of the interface f as shown in FIG. 14A. There are two possible deformations scenarios due to this force. In the first case, as shown in FIG. 14A, the substrate bends when either the upper or the lower surface alone is coated. This bending is similar to Stoney's observation of bending of nickel-plated metal strips due to residual stresses. In the second case, as seen in FIG. 14B, the substrate stretches when the same brush structure is present on both the upper and lower surfaces, leading to stretching without bending. In practice, it is difficult to ensure identical brush structure on the upper and lower surface. This leads to some bending. Consequently, both stretching and bending actuation of the substrate is possible with the polymer brush coatings.

Figure 15A:
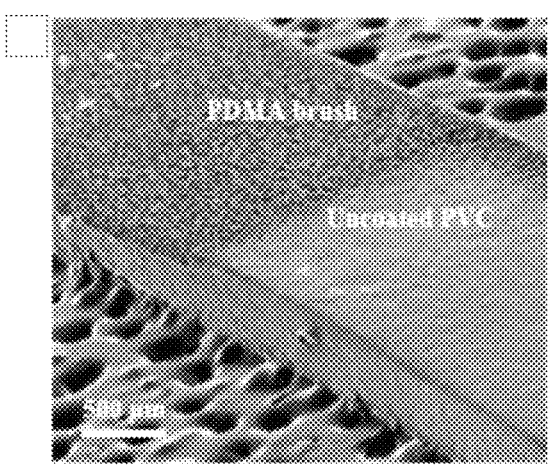
FIG. 15A is a representative SEM image of partial PDMA grafting on one side of pPVC.
Figure 15B:
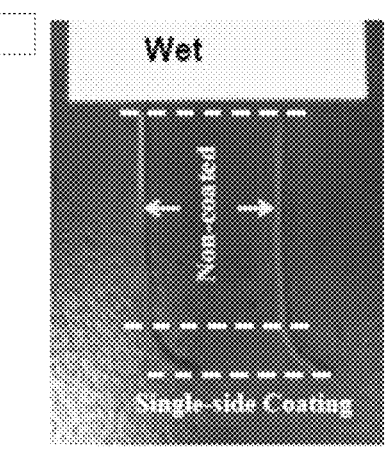
FIG. 15B is a representative SEM image of two wet specimens with partial PDMA grafting on a single side that was prepared from the same batch of SI-ATRP.

Consider bending actuation in which a pPVC beam is partially coated on one side and held such that one end is fixed while the other end is free to deform. FIGS. 15A and 15B depict a SEM morphology of a pPVC specimen with partial PDMA grafting one side. To prepare this specimen, only the desired area was treated with allylamine plasma and subsequent tethering of ATRP initiator.

FIG. 15A depicts a SEM image of partial PDMA grafting on one side of pPVC; FIG. 15B two wet specimen with partial PDMA grafting on single side were prepared from the same batch of SI-ATRP. Similar curvature was observed verifying the uniform coating and polymerization. The coated and uncoated lengths are denoted as $L_1$ and $L_2$, respectively in FIG. 7A. Every cross section within the coated/grafted region is subjected to a constant, internal bending moment, M, of magnitude $$M = \frac{fbt}{2}$$

about the mid-plane. Here, b and t denote the width and thickness of the pPVC substrate, respectively. Outside the coated region there is no bending moment. The deformed elastic curve can be obtained by solving the moment curvature relation for a thin Euler-Bernoulli beam together with the boundary conditions of zero displacement and rotation at the fixed end:

$$E_b I \frac{d^2 y}{dx^2} = M = \frac{fbt}{2} \qquad \text{eq. (1a)}$$

$$y(x=0) = 0 \text{ and } \left[\frac{dy}{dx}\right]_{x=0} = 0 \qquad \text{eq. (1b)}$$

Where $E_b$ is bi-axial Young's modulus related to the uni-axial Young's modulus E and Poisson ratio, θ, via the relation; I is the second moment of area of cross section about the mid-plane. For a specimen with rectangular cross-section, $$I = \frac{bt^3}{12}.$$

The solution of the above equations (1a) and (1b) gives the elastic deflection curve, y(x), of the substrate, from which the deflection, δ, at the free end=$L_1+L_2$, is given by $$\delta = \frac{fbt}{2EI} L_1 L_2 + \frac{fbt}{4EI} L_1^2 \qquad \text{eq. (2)}$$

which suggests that the tip deflection, δ, varies linearly with the uncoated length, $L_2$, and this linear variation is characterized by a slope to intercept ratio of $$\frac{2}{L_1}$$

in the δ-$L_2$ plane.

Figure 16:
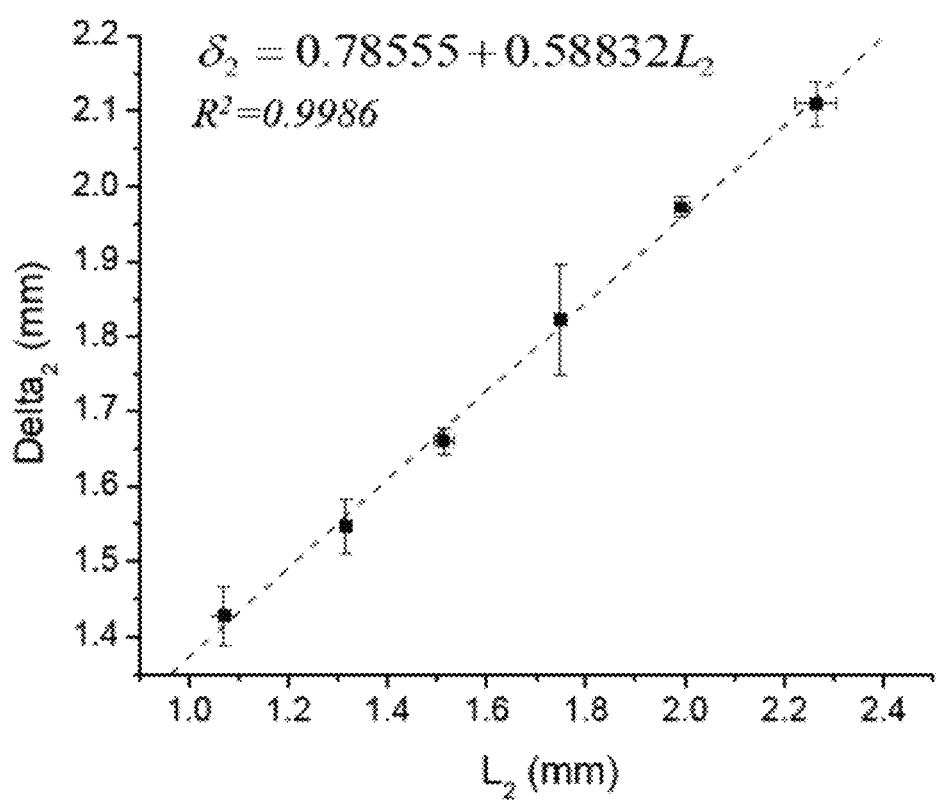
FIG. 16 is a graph showing the relationship of the uncoated length ($L_2$) with bending deformation $\delta_2$.
Figure 17:
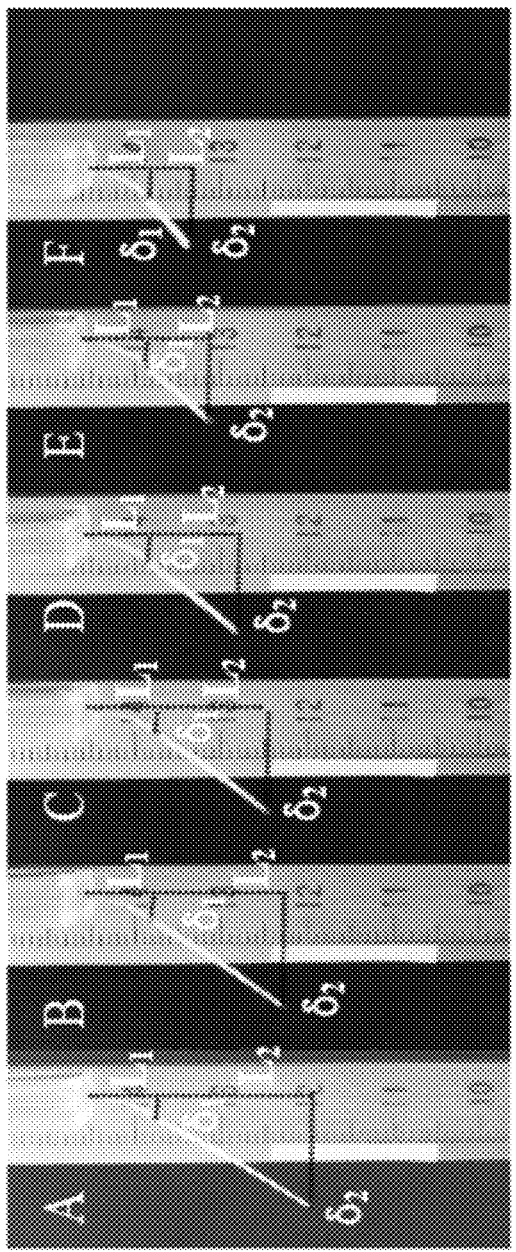
FIG. 17 is a representative photograph of a pPVC specimen with fixed coating length ($L_1$, one-side coating) which was gradually cut on the uncoated end to vary the uncoated length ($L_2$).

The measured tip deflection for different uncoated lengths, $L_2$, is shown in FIG. 16, which confirms the above linear variation prediction by our model. From these measurements, we estimate a membrane force of 24 N/m for a polymerization time of 4 hours and molecular weight 1,600,000 Da. FIG. 17 shows the pictures of the wet specimen for FIG. 16. $L_1$ (coating length) was fixed while $L_2$ (uncoated length) was gradually decreased. The correlation was then built between delta and $L_2$ as shown in FIG. 16.

When the specimen is coated on both sides by the same polymer brush structure, including grafted density and molecular weight, our model predicts no bending but a reversible stretching actuation. This is due to the fact that each cross section is subjected to a net longitudinal force of 2fb such that a change in the length of the substrate, $\Delta L$, results as shown in FIG. 14B, according to the relation $$\Delta L = \frac{2f}{tE} L \qquad \text{eq. (3)}$$

where the factor of 2 in the numerator follows from the assumption of the same membrane force per unit length on both the upper and lower surface. The above equation predicts that the change in length is proportional to the initial length, of the specimen before it is wetted.

In reality, it is difficult to obtain the same brush structure. This leads to unequal membrane forces on the upper and lower surfaces: $f_{upper} \neq f_{lower}$. Consequently, the specimen would bend as well as stretch. The radius of curvature of the bent specimen is given by:

$$R = \frac{f_{upper} - f_{lower}}{6E_b t^2} \qquad \text{eq. (4)}$$

and the change in length of the specimen is given by:

$$\Delta L = \frac{f_{upper} + f_{lower}}{tE} L.$$

A second set of experiments were conducted in which the initial (dry) length of a doubly coated pPVC specimen is varied, and for each length, the specimen is dipped in water and allowed to expand freely. The measured changes in length, did vary linearly according to the relation in equation (5). The estimated force per unit length for the upper and lower surfaces was 18.3 and 12.9 N/m, respectively. When the polymerization time was increased from 4 hours to 24 hours, much higher values of 74.7 and 67.3 N/m were deduced for the upper and lower surface, respectively (FIG. 18). This is attributed to the increase in grafted density with increase in polymerization time.

It is instructive to compare polymer brush actuator with other existing actuators based on two mechanical indices for actuator performance: (1) force per unit length and (2) actuator strain. The actuator force per unit length is deduced from the engineering analysis. Actuator strain is the maximum strain the actuator undergoes. The force per unit length versus actuator strain diagram is shown in FIG. 12E wherein actuators drawn from an actuator database are compared with polymer brush based actuators. It can be observed that there is a trade-off between force per unit length and actuator strain in general, for all actuators. Actuators with high force per unit length, such as piezoelectric materials, cannot provide large strains. Shape-memory metals such as Ni—Ti are attractive due to their larger strains. The polymer brush based actuators developed in this study are shown to provide even higher actuator strain (typically 10%) and moderate force per unit length slightly better than some electro-active polymers. This comparison diagram underlines the potential for polymer brush actuators in material systems. We note that grafted density and molecular weight govern the force per unit length and actuator strain, and the data reported here is for the experiments we conduced.

Evidently, the actuator strain, $$\varepsilon = \frac{\Delta L}{L}$$

depends on the material properties, Young's modulus E, and geometric properties: thickness t of the substrate as indicated by equation 4. Similarly, the force per unit length also depends on the membrane force per unit length, which in turn, depends on grafted density and molecular weight of the polymer brush structure. By varying the geometry and material properties of the substrate higher actuator strains can be achieved. Higher values for force per unit length are anticipated with changes in molecular weight and grafted density.

Example 5—Calculation of Bending Energy Based on the Bending Actuator Model

Calculations for bending energy can be based on bending actuation mechanism proposed in FIGS. 11C and 13A. Assuming a cubic polynomial function to approximate the deflection curve of the beam specimen, an estimate for the total elastic strain energy stored in bending deformation is obtained by evaluating the following integral:

$$U_{bending} = \int_0^{L_1} \frac{M^2}{2EI} dx = \frac{EI}{2} \int_0^{L_1} \left(\frac{d^2 y}{dx^2}\right)^2 dx \qquad \text{eq. (6a)}$$

$$U_{bending} = \frac{2EI}{L_1^3} (\Theta_1^2 L_1^2 - 3\delta_1 \Theta_1 L_1 + 3\delta_1^2). \qquad \text{eq. (6b)}$$

The invention claimed is:
1. A device comprising:
    a flexible substrate;
    a grafted polymer brush coating on at least one surface of the flexible substrate, wherein the grafted polymer brush coating is about 1 mm to about 10 cm in length and exerts a force on the flexible substrate to contract or bend in response to a stimulus; and
    at least one of the following: microelectromechanical systems (MEMS), piezoelectric technology, shaped-memory alloys (SMA), grafted polymers, stimuli producing elements, guide wires, and combinations thereof.
2. The device of claim 1, wherein the flexible substrate comprises polyester ethers, copolyester ethers, styrene based thermoplastic elastomers, olefin based thermoplastic elastomers, urethane based thermoplastic elastomers, ester based thermoplastic elastomers, amide based thermoplastic elastomers, polyolefines, natural rubber, synthetic rubber, poly(acrylates/methacrylates), synthetic hydrogels, natural hydrogels, silicone rubbers, and combinations thereof.

3. The device of claim 1, wherein the flexible substrate comprises a surface comprising functional groups selected from the group consisting of thiols, sulfides (—SR), disulfides (—SSR), wherein R is alkyl or aryl; tri-substituted silanes (—SiX$_3$), wherein X is halo, alkoxy, chloro, or methoxy; carboxylic acids; hydroxamic acids; acid chlorides; anhydrides; epoxides; peroxide groups; nitrile groups; thioester groups; alkoxamine groups; ester groups; haloester groups; sulfonyl groups; phosphoryl groups; hydroxyl groups; amino acid groups; amides; and combinations thereof.

4. The device of claim 1, wherein the grafted polymer brush coating comprises poly(ethylene glycol) methyl ether acrylate, poly(ethylene glycol) methyl ether methacrylate, poly(ethylene glycol) methyl ether acrylamide, poly(ethylene glycol) methyl ether methacrylamide, poly(vinyl methyl ether), poly(N-vinyl caprolactam), poly(N,N-dimethylacrylamide), poly(N-2,3-dihydroxylpropyl)acrylamide, poly(2,2-dimethyl-1,3 dioxalane)methyl] acrylamide, polydodecyl methacrylate (PDMA), dodecyl methacrylate (DMA), poly-n-butyl acrylate (PnBA), styrene/acrylonitrile copolymer (AS), polypropylenepolymethyl methacrylate (PMMA), acrylamide, N-acryloylmorpholine, 2-hydroxyethyl methacrylate (HEMA), N-isopropylacrylamide (NIPAM), 2-methoxyethyl acrylate (MEA), 2-methacryroyloxyethyl-phosphorylcholine (MPC), acrylamide/methacrylamide derivatives of carbohydrates, [3-(Methacryloylamino) propyl]dimethyl(3-sulfopropyl)ammonium hydroxide (SBMA), 1-vinyl-2-pyrrolidone (VP), basic monomers such as (3-acrylamidopropyl)trimethylammonium (APTA), allylamine (AA), 1,4-diaminobutane methacrylamide (DABMA), 2-acrylamido-2-methyl-1-propanesulfonic acid (AMPS), ethylene glycol methacrylate phosphate (EGMP), 2,2,2-trifluoroethyl methacrylate (TFEM), azobenzene containing copolymers of poly(ethyleneglycol) methacrylate, N-substituted acrylamides/methacrylamides (PAM), and combinations thereof.

5. The device of claim 1, further comprising micromachined polypyrrole (PPy), copper, or a combination thereof.

6. The device of claim 1, further comprising at least one force sensor, at least one piezoelectric tactile sensor, or combinations thereof.

7. The device of claim 1, further comprising at least one stent, therapeutic agent, ablation apparatus, fiber optic cameras, interferometry devices, spectroscopy devices, and combinations thereof.

8. A method for preparing a device, the method comprising:
providing a device comprising a flexible substrate;
applying a grafted polymer brush coating to at least one surface of the flexible substrate of the device, wherein the grafted polymer brush coating is about 1 mm to about 10 cm in length and exerts a force on the flexible substrate to contract or bend in response to a stimulus; and
attaching a stimuli producing element to the device adjacent to the grafted polymer brush coating.

9. The method of claim 8, further comprising connecting the stimuli producing element to a control module.

10. The method of claim 8, wherein the flexible substrate comprises polyester ethers, copolyester ethers, styrene based thermoplastic elastomers, olefin based thermoplastic elastomers, urethane based thermoplastic elastomers, ester based thermoplastic elastomers, amide based thermoplastic elastomers, polyolefines, natural rubber, synthetic rubber, poly(acrylates/methacrylates), synthetic hydrogels, natural hydrogels, silicone rubbers, and combinations thereof.

11. The method of claim 8, wherein the flexible substrate comprises a surface comprising functional groups selected from the group consisting of thiols, sulfides (—SR), disulfides (—SSR), wherein R is alkyl or aryl; tri-substituted silanes (SiX$_3$), wherein X is halo, alkoxy, chloro, or methoxy; carboxylic acids; hydroxamic acids; acid chlorides; anhydrides; epoxides; peroxide groups; nitrile groups; thioester groups; alkoxamine groups; ester groups; haloester groups; sulfonyl groups; phosphoryl groups; hydroxyl groups; amino acid groups; amides; and combinations thereof.

12. The method of claim 8, wherein the grafted polymer brush coating comprises poly(ethylene glycol) methyl ether acrylate, poly(ethylene glycol) methyl ether methacrylate, poly(ethylene glycol) methyl ether acrylamide, poly(ethylene glycol) methyl ether methacrylamide, poly(vinyl methyl ether), poly(N-vinyl caprolactam), poly(N,N-dimethylacrylamide), poly(N-2,3-dihydroxylpropyl)acrylamide, poly(2,2-dimethyl-1,3-dioxalane)methyl] acrylamide, polydodecyl methacrylate (PDMA), dodecyl methacrylate (DMA), poly-n-butyl acrylate (PnBA), styrene/acrylonitrile copolymer (AS), polypropylene-polymethyl methacrylate (PMMA), acrylamide, N-acryloylmorpholine, 2-hydroxyethyl methacrylate (HEMA), N-isopropylacrylamide (NIPAM), 2-methoxyethyl acrylate (MEA), 2-methacryroyloxyethyl-phosphorylcholine (MPC), acrylamide/methacrylamide derivatives of carbohydrates, [3-(Methacryloylamino) propyl]dimethyl(3-sulfopropyl)ammonium hydroxide (SBMA), 1-vinyl-2-pyrrolidone (VP), basic monomers such as (3-acrylamidopropyl)trimethylammonium (APTA), allylamine (AA), 1,4-diaminobutane methacrylamide (DABMA), 2 acrylamido-2-methyl-1-propanesulfonic acid (AMPS), ethylene glycol methacrylate phosphate (EGMP), 2,2,2-trifluoroethyl methacrylate (TFEM), azobenzene containing copolymers of poly(ethyleneglycol) methacrylate, N-substituted acrylamides/methacrylamides (PAM), and combinations thereof.

13. The device of claim 1, wherein the device comprises one or more stimuli producing elements configured to provide the stimulus to the grafted polymer brush coating.

14. The device of claim 1, wherein the stimuli producing elements include a heating element configured to provide the stimulus to the grafted polymer brush coating.

15. The device of claim 1, wherein the stimuli producing element comprises a lumen configured to provide a liquid stimulus to the grafted polymer brush coating.

16. The device of claim 1, further comprising a control module capable of activating the at least one of the following: microelectromechanical systems (MEMS), piezoelectric technology, shaped-memory alloys (SMA), grafted polymers, stimuli producing elements, guide wires, and combinations thereof.

17. The device of claim 1, further comprising at least one reservoir capable of delivering at least one therapeutic agent to the device.

18. The device of claim 1, wherein the device is one or more of a catheter tip and a catheter.

19. The method of claim 8, wherein attaching the stimuli producing element comprises attaching one or more of a heating element configured to provide heat and a lumen configured to deliver a liquid.

20. The method of claim 8, wherein applying the grafted polymer brush coating comprises modifying the surface of the flexible substrate and binding the grafted polymer brush coating to the substrate.

* * * * *